US012357619B2

(12) United States Patent
Ivachtchenko et al.

(10) Patent No.: US 12,357,619 B2
(45) Date of Patent: Jul. 15, 2025

(54) NORADRENERGIC AND SPECIFIC SEROTONERGIC ANXIOLYTIC AND ANTIDEPRESSANT, METHOD FOR THE PRODUCTION AND USE THEREOF

(71) Applicants: ALLA CHEM, LLC, Hallandale, FL (US); Alena Alexandrovna Ivachtchenko, Hallandale, FL (US); Nikolay Filippovich Savchuk, Rancho Santa Fe, CA (US)

(72) Inventors: Alexandre Vasilievich Ivachtchenko, Hallandale Beach, FL (US); Andrey Alexandrovich Ivashchenko, Moscow (RU)

(73) Assignees: ALLA CHEM LLC, Hallandale, FL (US); Alena Alexandrovna Ivachtechenko, Hallandale, FL (US); Nikolay Filippovich Savchuk, Rancho Santa Fe, CA (US)

( * ) Notice: Subject to any disclaimer, the term of this patent is extended or adjusted under 35 U.S.C. 154(b) by 0 days.

(21) Appl. No.: 16/767,155

(22) PCT Filed: Mar. 27, 2020

(86) PCT No.: PCT/RU2020/000161
§ 371 (c)(1),
(2) Date: Jun. 26, 2023

(87) PCT Pub. No.: WO2021/187997
PCT Pub. Date: Sep. 23, 2021

(65) Prior Publication Data
US 2024/0238260 A1    Jul. 18, 2024

(30) Foreign Application Priority Data
Mar. 19, 2020  (RU) ................................ 2020111367

(51) Int. Cl.
C07D 471/04    (2006.01)
A61K 31/437    (2006.01)
A61P 25/22    (2006.01)
A61P 25/24    (2006.01)

(52) U.S. Cl.
CPC ............ *A61K 31/437* (2013.01); *A61P 25/22* (2018.01); *A61P 25/24* (2018.01); *C07D 471/04* (2013.01)

(58) Field of Classification Search
CPC ..... C07D 471/04; A61K 31/437; A61P 25/22; A61P 25/24; A51K 31/437
USPC ............................................ 546/84; 514/292
See application file for complete search history.

(56) References Cited

U.S. PATENT DOCUMENTS 8,338,408 B2 * 12/2012 Hung ........................ A61P 9/00
544/251

FOREIGN PATENT DOCUMENTS

RU    2020111367    3/2020

OTHER PUBLICATIONS

Ivachtchenko, A.V. et al.: AVN-101 : A multi-target drug candidate for the treatment of CNS disorders. Journal of Alzheimer's disease, vol. 53, pp. 583-620, 2016.*

* cited by examiner

*Primary Examiner* — Charanjit Aulakh
(74) *Attorney, Agent, or Firm* — Paul D. Strain, Esq.; Strain & Strain PLLC

(57) ABSTRACT

The present invention relates to a novel Noradrenergic and Specific Serotonergic Anxiolytic and Antidepressant (NaSSA) and a method for the production and use thereof for treating mental disorders.

Figure 1:
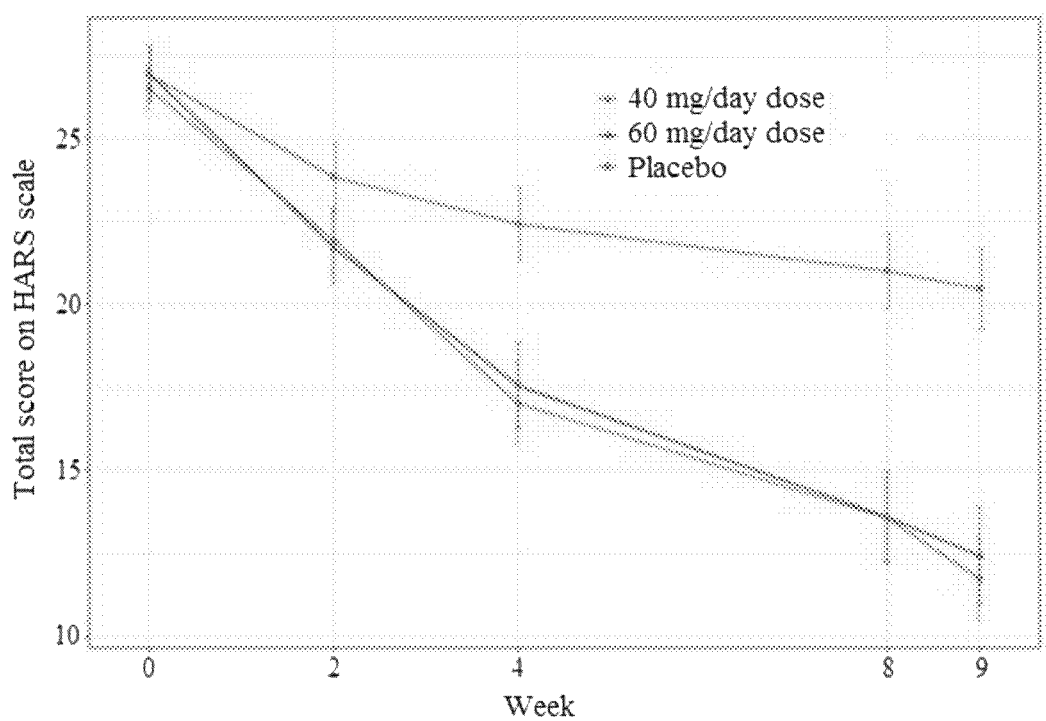

The subject of this invention is a novel noradrenergic and specific serotonergic drug for the treatment of mental disorders in humans, which is 2,8-dimethyl-5-(2-phenylethyl)-2,3,4,5-tetrahydro-1H-pyrido[4,3-b]indole hydrochloride (A·HCl), a polymorphous modification thereof, and methods for the production and use thereof.

18 Claims, 9 Drawing Sheets

NORADRENERGIC AND SPECIFIC SEROTONERGIC ANXIOLYTIC AND ANTIDEPRESSANT, METHOD FOR THE PRODUCTION AND USE THEREOF

CROSS-REFERENCE TO RELATED PATENT APPLICATIONS

This application is a National Stage of International Application No. PCT/RU2020/000161, filed Feb. 14, 2018, which is based upon and claims the benefit of priority from prior Russian Patent Application No. 2020111367, filed Mar. 27, 2020, the entire contents of all of which are incorporated herein by reference in their entirety.

FIELD OF THE INVENTION

The present invention relates to a novel Noradrenergic and Specific Serotonergic Anxiolytic and Antidepressant (NaSSA) and a method for the production and use thereof for treating mental disorders.

BACKGROUND OF THE INVENTION

Common mental disorders are increasing worldwide. Between 1990 and 2013, the number of people suffering from depressions and/or anxiety increased by nearly 50%, from 416 million to 615 million. Close to 10% of the world's population is affected, and mental disorders account for 30% of the global non-fatal disease burden. Humanitarian emergencies and ongoing conflict add further to the need for scale-up of treatment options. WHO estimates that, during emergencies, as many as 1 in 5 people are affected by depression and anxiety. Depression and anxiety disorders cost the global economy US$1 trillion each year [https://www.who.int/ru/news-room/detail/13-04-2016-investing-in-treatment-for-depression-and-anxiety-leads-to-fourfold-return].

Over the past decades, psychopharmacotherapy has made steady progress, new drugs to treat mental illnesses have appeared. Today, the choice of psychotropic medications (PMs) is extremely relevant for patients treated not only at mental health clinics, but also in general medical practice. This is due to the widespread prevalence of anxiety and depression among the population (in Russia, up to 6-7%) and its steady growth, frequent combination of mental and somatic pathologies, for which reason doctors of various specialties are faced with the need to use PMs. It is they, rather than neurologists or psychiatrists, who prescribe ⅔ of all PMs. As a result, according to WHO, about ⅓ of the adult population of developed countries take psychopharmacological drugs (in the absence of hypodiagnosis, this figure could be even higher) [https://www.rmj.ru/articles/psikhiatriya/Antidepressanty_1_anksiolitiki preimuschestva_1_nedostatki/].

Anxiety and depressive disorders are highly associated with the disease and have overlapping manifestations of symptoms. Indeed, more than half (58%) of all patients with major depressive disorder (MDD) have an anxiety disorder, including generalized anxiety disorder (GAD).

Pharmacotherapy for the treatment of major depressive disorders has been available since the introduction of tricyclic antidepressants (TCA) and monoamine oxidase inhibitors (MAOI) in the 1950s. The first selective serotonin reuptake inhibitors (SSRIs) were introduced in the 1980s, and due to their improved safety and tolerability profiles compared to TCA and MAOI, they have become the most widely prescribed drugs for the treatment of depression and related disorders. Serotonin and norepinephrine reuptake inhibitors (SNRI) entered the market in the 1990s.

SSRIs and SNRIs are considered to be first-line therapy and are effective in both anxiety and depressive states. However, patients suffering from depression and having high levels of anxiety usually exhibit more severe symptoms, a weaker response to treatment, and greater sensitivity to side effects than patients suffering from depression without an anxiety disorder. These factors contribute to an increased frequency of treatment discontinuation and significant unmet needs [Richelson E. Multi-modality: a new approach for the treatment of major depressive disorder. SSRIs/SNRIs *Intern. J. Neuropsychopharmacology* 2013, 16(6), 1433-1442].

In the 1990s, psychiatric drugs belonging to the class of noradrenergic and specific serotonergic anxiolytics and antidepressants (NaSSA) entered the market. They act by antagonizing the adrenergic and serotonin receptors.

The typical and most effective representative of NaSSA is Mirtazapine sold under the brand names Remeron, Norset, Avanza, Zispin, etc. Mirtazapine was first approved for use in depressive disorders in the Netherlands in 1994, and in 1996 in the United States under the brand name Remeron [https://en.wikipedia.org/wiki/Mirtazapine]. Mirtazapine is the most effective and safe drug compared to classic drugs of other classes (TCAs, SSRIs and SNRIs) [S.-M. Wang et al. Addressing the Side Effects of Contemporary Antidepressant Drugs: A Comprehensive Review. Chonnam Med. J. 2018, 54(2), 101-112].

Mirtazapine is used for depression complicated by anxiety or sleep problems [Anttila S. A., Leinonen E. V. A review of the pharmacological and clinical profile of mirtazapine. CNS Drug Rev. 2001, 7 (3), 249-264. Nutt D. J. Tolerability and safety aspects of mirtazapine. *Hum. Psychopharmacol.* 2002, 17 Suppl 1, S37-41.]. It also has a strong antihistamine effect [Mirtazapine Monograph for Professionals. Drugs-.com. American Society of Health-System Pharmacists. 2018].

Common side effects include weight gain, drowsiness, and dizziness [8]. Serious side effects may include mania, low white blood cell count, and an increased number of suicides among children. Withdrawal symptoms may occur when therapy is stopped [British national formulary: BNF 74 (74 ed.). *British Medical Association*. 2017, p. 354. ISBN 978-0857112989.]. It is unclear whether it is safe to use Mirtazapine during pregnancy [Mirtazapine Monograph for Professionals. Drugs.com. American Society of Health-System Pharmacists. 2018]. In this regard, the creation of new NaSSA drugs that have fewer side effects than Mirtazapine is an urgent task.

Listed below are definitions of various terms used to describe this invention. These definitions apply to the terms as they are used throughout this specification and claims, unless otherwise limited in specific instances, either individually or as part of a larger group.

The term "crystalline form" refers to a substance structure wherein the molecules are arranged to form a crystal lattice.

The term "polycrystalline form" refers to a polycrystalline substance structure consisting of a plurality of small monocrystals with various lattice forms.

The term "active ingredient" (drug substance) refers to a physiologically active compound of synthetic or other origin, which exhibits pharmacological activity and is the active ingredient of a pharmaceutical composition.

The term "pharmaceutical composition" refers to a composition comprising the active ingredient and at least one excipient selected from the group consisting of pharmaceutically acceptable and pharmacologically compatible fillers, solvents, diluents, carriers, excipients, distributing and receptive agents, delivery agents such as preservatives, stabilizers, fillers, disintegrators, moisteners, emulsifiers, suspending agents, thickeners, sweeteners, flavoring agents, aromatizing agents, antibacterial agents, fungicides, lubricants, and prolonged delivery controllers, the choice and proportions of which depend on the nature and route of administration and dosage. Examples of suitable suspending agents are ethoxylated isostearyl alcohol, polyoxyethylene, sorbitol and sorbitol ether, microcrystalline cellulose, aluminum metahydroxide, bentonite, agar-agar and tragacanth, and mixtures thereof. Protection against microorganisms can be provided using various antibacterial and antifungal agents, such as parabens, chlorobutanol, sorbic acid, and the like. Said composition may also include isotonic agents, such as sugar, sodium chloride, and the like. The sustained action of the composition can be achieved using agents that decelerate the absorption of the active ingredient, for example, aluminum monostearate and gelatin. Examples of suitable carriers, solvents, diluents, and delivery agents include water, ethanol, polyalcohols and mixtures thereof, natural oils (such as olive oil), and organic esters (such as ethyl oleate) for injections. Examples of fillers are lactose, milk sugar, sodium citrate, calcium carbonate, calcium phosphate, and the like. Examples of disintegrators and distributors are starch, alginic acid and salts thereof, and silicates. Examples of lubricants are magnesium stearate, sodium lauryl sulfate, talc, and polyethylene glycol of high molecular weight. A pharmaceutical composition for peroral, sublingual, transdermal, intramuscular, intravenous, subcutaneous, and local or rectal administration of the active ingredient, alone or in combination with another active compound, can be administered to animals and people in a standard administration form as a mixture with traditional pharmaceutical carriers.

The term "excipient" as used herein refers to a compound that is used to produce a pharmaceutical composition and is generally safe and non-toxic and comprises substances acceptable for use in medicine. Active ingredients can be administered individually to humans or animals, but they are usually administered in a mixture with one or more pharmaceutically acceptable agents (excipients, diluents, or carriers) selected based on the intended route of administration and standard therapy.

The term "medicinal drug" refers to a compound (or a mixture of compounds forming a pharmaceutical composition) in finished dosage forms intended for the restoration, improvement, or modification of physiological functions in humans and animals, and for the treatment and prophylaxis of diseases, for diagnostics, anesthesia, contraception, cosmetology, etc. Suitable standard administration forms include peroral forms, such as tablets, gelatin capsules, pills, powders, granules, chewing gums, and peroral solutions or suspensions; sublingual and transbuccal administration forms; aerosols; implants; local, transdermal, subcutaneous, intramuscular, intravenous, intranasal, or intraocular forms; and rectal administration forms.

The term "therapeutically effective amount," as used herein, refers to an amount of an active ingredient needed for alleviating the symptoms of the disease in the subject. The dose of the active ingredient will meet individual demands in each particular case. Said dose may vary in a wide range depending on numerous factors like activity and bioavailability thereof, the severity of the disease to be treated, the age and the general condition of the patient, other medicaments used for the patient's treatment, the mode and route of administration, and the experience of the attending doctor. For oral administration, the daily dose is approximately 0.01-10 g, including all values therebetween, both in monotherapy and/or combination therapy. The preferred daily dose is around 0.01-1 g.

The term "subject" refers to a mammal that includes, but is not limited to, cattle, pigs, sheep, chickens, turkeys, buffaloes, llamas, ostriches, dogs, cats, and humans, preferably the subject is a human.

The term "patient" refers to a person receiving medical care, undergoing medical supervision and/or treatment for any disease, pathological condition or other health or life disorders, as well as using medical services, regardless of whether they have a disease.

SUMMARY OF THE INVENTION

It is known that 2,8-dimethyl-5-(2-phenylethyl)-2,3,4,5-tetrahydro-1H-pyrido[4,3-b]indole (A), its pharmaceutically acceptable salt and/or hydrate is an antagonist of 5-HT6 serotonin receptors, simultaneously regulating the homeostasis of calcium ions in cells [Patent RU 2334747, 2008]. It is also known that the spectrum of biological activity of this ligand (A) includes simultaneously α-adrenoceptors, dopamine receptors, histamine receptors, imidazoline receptors and serotonin receptors [Patent RU 2407744, 2010. A. V. Ivachtchenko at. al. AVN-101: A Multi-Target Drug Candidate for the Treatment of CNS Disorders. Alzh. Disease 53 (2016) 583-620.].

Based on the study of the activity of this ligand in mouse models, a drug and a method have been proposed for the treatment and/or prevention of CNS diseases and pathological conditions, the pathogenesis of which is associated with hyper- or hypo-activation of simultaneously α-adrenoceptors, dopamine receptors, histamine H2 receptors, imidazoline receptors and groups 5-HT1A, 5-HT1B, 5-HT2A, 5-HT2B, 5-HT2C, 5-HT7 serotonin receptors, by administration of pharmacologically effective amount of 2,8-dimethyl-5-(2-phenylethyl)-2,3,4,5-tetrahydro-1H-pyrido[4,3-b]indole [Patent RU 2407744, 2010].

However, there is no data in scientific and patent literature on the use of said ligand as a noradrenergic and specific serotonergic drug for treating CNS disorders in people who need it.

The inventors have surprisingly found that 2,8-dimethyl-5-(2-phenylethyl)-2,3,4,5-tetrahydro-1H-pyrido[4,3-b]indole hydrochloride, its polymorphic modification (PM), in humans not show side effects that characterize ligands possessing activity against dopamine, histamine and imidazoline receptors.

The subject of this invention is a novel noradrenergic and specific serotonergic drug for the treatment of mental disorders in humans, which is a 2,8-dimethyl-5-(2-phenylethyl)-2,3,4,5-tetrahydro-1H-pyrido[4,3-b]indole hydrochloride (A·HCl), its polymorphic modification, and methods for preparation and application thereof.

The subject of this invention is a novel noradrenergic and specific serotonergic drug for the treatment of mental disorders in humans, which is a polymorphic modification (PM-1) of 2,8-dimethyl-5-(2-phenylethyl)-2,3,4,5-tetrahydro-1H-pyrido[4,3-b]indole hydrochloride (A·HCl) in the form of rhombic crystals characterized by the crystallographic group Pbca.

The subject of this invention is a novel noradrenergic and specific serotonergic drug for the treatment of mental disorders in humans, which is a polymorphic modification (PM-2) of 2,8-dimethyl-5-(2-phenylethyl)-2,3,4,5-tetrahydro-1H-pyrido[4,3-b]indole (A·HCl) hydrochloride in the form of rhombic crystals characterized by the crystallographic group Pnnn.

The subject of this invention is a previously unknown polymorphic modification (PM-1) of 2,8-dimethyl-5-(2-phenylmethyl)-2,3,4,5-tetrahydro-1H-pyridol[4,3-b]indole hydrochloride (A·HCl) in the form of rhombic crystals characterized by the crystallographic group Pbca; The subject of this invention is a previously unknown polymorphic modification (PM-1) of 2,8-dimethyl-5-(2-phenylmethyl)-2,3,4,5-tetrahydro-1H-pyridol[4,3-b]indole hydrochloride (A·HCl) in the form of rhombic crystals characterized by the crystallographic group Pnnn;

The subject of this invention is a previously unknown mixture of polymorphic modifications of 2,8-dimethyl-5-(2-phenylmethyl)-2,3,4,5-tetrahydro-1H-pyridol[4,3-b]indole hydrochloride (A·HCl), which is a mixture of rhombic crystals PM-1 and/or PM-2 and amorphous phase.

A process known to produce 2,8-dimethyl-5-(2-phenylethyl)-2,3,4,5-tetrahydro-1H-pyrido[4,3-b]indole (A) involves:
(a)-synthesis of 2,8-dimethyl-2,3,4,5-tetrahydro-1H-pyridone[4,3-b]indole (A3) with a 52% yield by interaction of p-tolylhydrazine (A1) with N-methylpiperidone-4 (A2) in dioxane at 80° C. (Scheme 1) [WO/2010/051501];

Scheme 1. Synthesis of 2,8-dimethyl-2,3,4,5-tetrahydro-1H-pyridone[4,3-b]indole (A3).

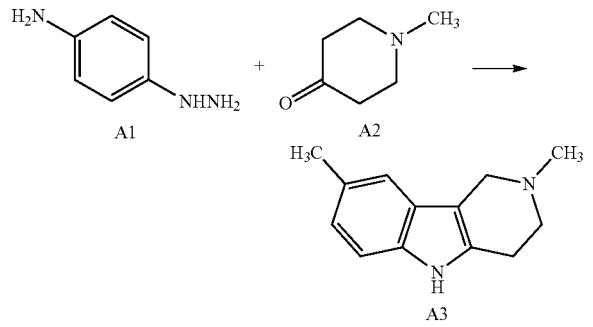

(6)-synthesis of 2,8-dimethyl-5-(2-phenylethyl)-2,3,4,5-tetrahydro-1H-pyrido[4,3-b]indole (A) by interaction of carboline A3 with phenylacetylene (A4) in 1 ml of dimethylsulfoxide, in the presence of 3 ml of 60% aqueous KOH and 100 ml of 50% aqueous (Bu4N)2SO4 for 6-12 hours at 20-80° C. and subsequent hydrogenation on a platinum catalyst formed 2,8-dimethyl-5-(2-phenylethenyl)-2,3,4,5-tetrahydro-1H-pyrido[4,3-b]indole (A5) and (scheme 2). Upon completion of the reaction, the reaction mass is filtered or centrifuged, the filtrate is evaporated in vacuum, and the residue is chromatographed on a triethylamine impregnated silica gel (eluent: chloroform-triethylamine or dichloromethane-tetrahydrofuran-triethylamine) or recrystallized from a suitable solvent (no solvent specified). The method for preparing 2,8-dimethyl-5-(2-phenylethyl)-2,3,4,5-tetrahydro-1H-pyrido[4,3-b]indole (A·HCl) hydrochloride is not provided in the specified patents. The patents also lack data on the phase form of the resulting 2,8-dimethyl-5-(2-phenylethyl)-2,3,4,5-tetrahydro-1H-pyrido[4,3-b]indole (A) and its salts or x-ray phase data confirming the polymorphic modification of 2,8-dimethyl-5-(2-phenylethyl)-2,3,4,5-tetrahydro-1H-pyrido[4,3-b]indole samples obtained (a) [Patents RU 2334747 (2008), RU 2407744 (2010)].

Scheme 2. Synthesis of 2,8-dimethyl-5-(2-phenylethyl)-2,3,4,5-tetrahydro-1H-pyrido[4,3-b]indole (A) and its hydrochloride A·HCl.

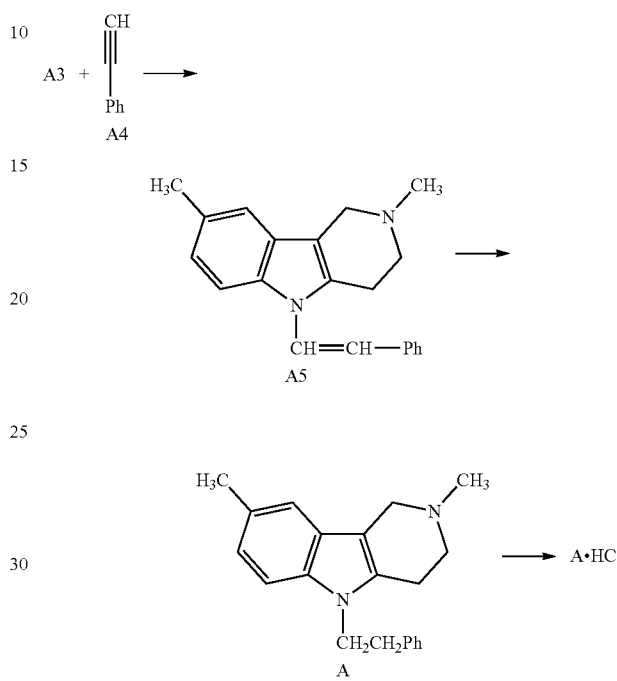

The subject of this invention is a method for the production of 2,8-dimethyl-5-(2-phenylethyl)-2,3,4,5-tetrahydro-1H-pyrido[4,3-b]indole (A) by the interaction of 4-methylphenylhydrazine hydrochloride (A1·HCl) with styrene (A6) and the interaction of the resulting 1-(4-methylphenyl)-1-(2-phenylethyl)hydrazine hydrochloride (A7·HCl with 1-methylpiperidin-4-one (A2 followed by transforming, if necessary, the reaction product (A·HCl) into the base (A) and then, if necessary, into another pharmaceutically acceptable salt (Scheme 3).

Scheme 3. Synthesis of 2,8-dimethyl-5-(2-phenylethyl)-2,3,4,5-tetrahydro-1H-pyrido[4,3-b]indole (A) and its hydrochloride A·HCl.

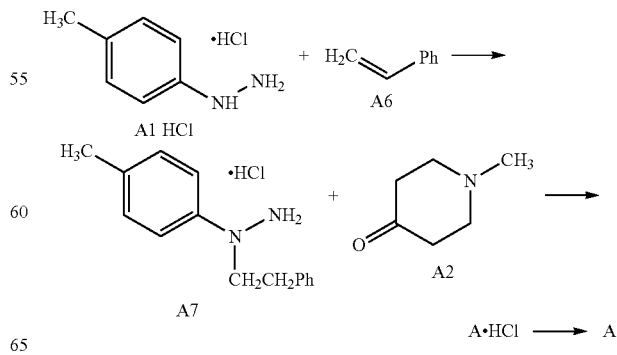

The novel method for the production of 2,8-dimethyl-5-(2-phenylethyl)-2,3,4,5-tetrahydro-1H-pyrido[4,3-b]indole hydrochloride (A·HCl) is simpler, shorter in duration, and does not require the use of an expensive platinum catalyst as compared to the known method [Patents RU 2334747 (2008), RU 2407744 (2010)].

The subject of this invention is a method for producing a polymorphic modification (PM-1) 2,8-dimethyl-5-(2-phenylethyl)-2,3,4,5-tetrahydro-1H-pyrido[4,3-b]indole hydrochloride (A·HCl) in the form of rhombic crystals characterized by the by a crystallographic group PBC by recrystallization of A·HCl from isopropanol.

The subject of this invention is a method for producing a polymorphic modification (PM-2) 2,8-dimethyl-5-(2-phenylethyl)-2,3,4,5-tetrahydro-1H-pyrido[4,3-b]indole hydrochloride (A·HCl) in the form of rhombic crystals characterized by the by a crystallographic group Pnnn by recrystallization of A·HCl from ethanol.

The subject of this invention is a method for producing a PM-1 mixture and/or a PM-2 mixture and the amorphous phase of 2,8-dimethyl-5-(2-phenylethyl)-2,3,4,5-tetrahydro-1H-pyrido[4,3-b]indole hydrochloride (A·HCl) in the form of rhombic crystals characterized by the by crystallographic groups Pbca and/or Pnnn and the amorphous phase by recrystallization of A·HCl from water or aqueous ethanol.

The subject of this invention is a novel noradrenergic and specific serotonergic drug for the treatment of mental disorders in people, which is 2,8-dimethyl-5-(2-phenylethyl)-2,3,4,5-tetrahydro-1H-pyrido[4,3-b]indole hydrochloride (A·HCl), its polymorphic modification or a mixture of polymorphic modification(s) and amorphous phase in in a therapeutically effective amount.

The preferred drug is PM-1, PM-2, or a mixture of PM-1 and/or PM-2 and the amorphous phase of 2,8-dimethyl-5-(2-phenylethyl)-2,3,4,5-tetrahydro-1H-pyrido[4,3-b]indole hydrochloride (A·HCl) in a therapeutically effective amount.

A further subject of this invention is the active ingredient of pharmaceutical compositions, which is a noradrenergic and specific serotonergic drug of this invention in a therapeutically effective amount.

The active ingredient of this invention as compared to the drug prototype

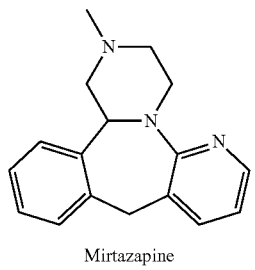 [SMILES: CN1CCN2c3ncccc3Cc3ccccc3C2C1]

Mirtazapine

Mirtazapine has a significantly higher activity against adrenergic and specific serotonin receptors (Table 1)

TABLE 1

Activities of A•HCl of this invention and Mirtazapine

| Receptors | A•HCl, $K_i$, nM | Mirtazapine[a], $K_i$, nM |
|---|---|---|
| Adrenergic $\alpha_{1A}$ | 30.2 | 316-1815 |
| Adrenergic $\alpha_{2A}$ | 1.77 | 20 |
| Adrenergic $\alpha_{2B}$ | 0.41 | 88 |

TABLE 1-continued

Activities of A•HCl of this invention and Mirtazapine

| Receptors | A•HCl, $K_i$, nM | Mirtazapine[a], $K_i$, nM |
|---|---|---|
| Adrenergic $\alpha_{2C}$ | 3.55 | 18 |
| Serotonin 5-HT$_{1A}$ | 61 | 3330-5100 |
| Serotonin 5-HT$_{2A}$ | 1.56 | 6.3-69 |
| Serotonin 5-HT$_{2B}$ | 10.6 | 200 |
| Serotonin 5-HT$_{2C}$ | 1.17 | 8.9-39 |
| Serotonin 5-HT$_6$ | 2.04 | ND |
| Serotonin 5-HT$_7$ | 0.153 | 265 |
| Histamine H$_1$ | 0.58 | 0.14-1.6 |

[a]https://en.wikipedia.org/wiki/Mirtazapine

A still further subject of this invention is a pharmaceutical composition in tablets, capsules, pills, powders, granules, chewing gums, and peroral solutions or suspensions, aerosols, implants, and subcutaneous, intramuscular, intravenous, and intranasal forms, said composition comprising a pharmaceutically effective amount of the active ingredient of this invention and optionally excipients.

The subject of this invention is a pharmaceutical composition in tablets, capsules, pills, powders, granules, chewing gums, and peroral solutions or suspensions, aerosols, implants, and subcutaneous, intramuscular, intravenous, and intranasal forms, said composition comprising, as the active ingredient, a pharmaceutically effective amount of PM-1 in the form of rhombic crystals characterized by the crystallographic group Pbca.

The subject of this invention is a pharmaceutical composition in tablets, capsules, pills, powders, granules, chewing gums, and peroral solutions or suspensions, aerosols, implants, and subcutaneous, intramuscular, intravenous, and intranasal forms, said composition comprising, as the active ingredient, a pharmaceutically effective amount of PM-2 in the form of rhombic crystals characterized by the crystallographic group Pnnn.

The subject of this invention is a pharmaceutical composition in tablets, capsules, pills, powders, granules, chewing gums, and peroral solutions or suspensions, aerosols, implants, and subcutaneous, intramuscular, intravenous, and intranasal forms, said composition comprising, as the active ingredient, a pharmaceutically effective amount of a mixture of PM-1 and/or PM-2 and the amorphous phase of 2,8-dimethyl-5-(2-phenylethyl)-2,3,4,5-tetrahydro-1H-pyrido[4,3-b]indole hydrochloride (A·HCl).

Excipients are generally selected from pharmacologically compatible distributing and receptive agents, delivery agents such as preservatives, stabilizers, fillers, disintegrators, moisteners, emulsifiers, suspending agents, thickeners, sweeteners, flavoring agents, aromatizing agents, antibacterial agents, fungicides, lubricants, and prolonged delivery controllers, the choice and proportions of which depend on the nature and method of administration, and the pharmaceutical composition. Examples of suitable suspending agents are ethoxylated isostearyl alcohol, polyoxyethylene, sorbitol and sorbitol ether, microcrystalline cellulose, aluminum metahydroxide, bentonite, agar-agar and tragacanth, and mixtures thereof. Protection against microorganisms can be provided using various antibacterial and antifungal agents, such as parabens, chlorobutanol, sorbic acid, and the like. Said composition may also include isotonic agents, such as sugar, sodium chloride, and the like. The sustained action of the composition can be achieved using agents that decelerate the absorption of the active ingredient, for example, aluminum monostearate and gelatin. Examples of suitable carriers, solvents, diluents and delivery agents include water, ethanol, polyalcohols and mixtures thereof, natural oils (such as olive oil), and organic esters (such as ethyl oleate) for injections. Examples of fillers are lactose, milk sugar, sodium citrate, calcium carbonate, calcium phosphate, and the like. Examples of disintegrators and distributors are starch, alginic acid and salts thereof, and silicates. Examples of lubricants are magnesium stearate, sodium lauryl sulfate, talc, and polyethylene glycol of high molecular weight. A pharmaceutical composition for peroral, sublingual, transdermal, intramuscular, intravenous, subcutaneous, and local or rectal administration of the active ingredient, alone or in combination with another active compound, may be administered to animals and people in a standard administration form as a mixture with traditional pharmaceutical carriers. Suitable standard administration forms include peroral forms, such as tablets, gelatin capsules, pills, powders, granules, chewing gums, and peroral solutions or suspensions; sublingual and transbuccal administration forms; aerosols; implants; local, transdermal, subcutaneous, intramuscular, intravenous, intranasal, or intraocular forms; and rectal administration forms.

The pharmaceutical composition of this invention preferably is a capsule, a tablet, a pill, powder, granules, a chewing gum, a solution, or a suspension.

The pharmaceutical composition of this invention preferably contains from 2.2% to 17.2% of the active ingredient of this invention, with pharmaceutically acceptable excipients comprising the remaining percentage.

The subject of this invention is a pharmaceutical composition in tablet form comprising from 2.2% to 11.1% or from 2.2% to 17.2% of the active ingredient of this invention, with pharmaceutically acceptable excipients comprising the remaining percentage.

For excipients, the pharmaceutical composition in tablet form contains, for example, fillers (lactose and microcrystalline cellulose 101), a free flow agent (Aerosil 200), a suspending agent (polyvinylpyrrolidone), and a lubricant (calcium stearate). The tablet can be coated with a Colorcon Acryl-EZE slow-release acrylic enteric film.

The subject of the present invention is a pharmaceutical composition in capsule form comprising from 2.2% to 17.2% of the active ingredient of this invention, with pharmaceutically acceptable excipients comprising the remaining percentage.

For excipients, the pharmaceutical composition in capsule form contains, for example, fillers (lactose and microcrystalline cellulose 101), a free flow agent (Aerosil 200), a suspending agent (polyvinylpyrrolidone), leavening agent (sodium starch glycolate) and lubricant (calcium stearate) or, for example, fillers (lactose and microcrystalline cellulose 101), enterosorbent (silicon dioxide colloidal), lubricant (hydrogenated castor oil and magnesium stearate) and leavening agent (potato starch 6%).

The subject of this invention is the use of the pharmaceutical composition in the form of a tablet, capsule, pill, powder, granule or chewing gum including, in a therapeutically effective amount, the active ingredient of this invention, as an oral drug.

The subject of this invention is an oral drug, which is a pharmaceutical composition in the form of a tablet, capsule, pill, powder, granule, or chewing gum, comprising the active ingredient of this invention in a therapeutically effective amount.

Another subject of this invention is the use, in a therapeutically effective amount, of the active ingredient of this invention and pharmaceutical compositions based thereon in the treatment of diseases of the Central Nervous System (CNS).

The subject of this invention is the use of the pharmaceutical composition of this invention in the treatment of CNS disorders in patients in need thereof, including anxiety disorders and depressions.

The subject of this invention is a method for treating and/or preventing CNS disorders in patients in need thereof, including anxiety disorders and depressions, characterized by administration to the patient of the pharmaceutical composition of this invention in a therapeutically effective amount.

The preferred method of treatment and/or prophylaxis of CNS disorders in patients in need thereof, including anxiety disorders and depressions, which according to Claim this invention is characterized by administering to the patient the pharmaceutical composition of this invention at a dose of the active ingredient varying from 2 mg/day to 60 mg/day (as A base).

The dose of the active ingredient of this invention depends on a patient's disease status, age, or weigh. The dose may be administered once a day or divided into several daily doses. The compound of his invention can be used in combination with other medicaments (hereinafter referred to as combination therapy) to enhance the drug's activity, to reduce the compound's dose, and the like.

A study of the pharmacokinetics and safety of single and multiple increasing doses of the active ingredient (2 mg, 4 mg, 10 mg, 20 mg as base) and multiple increasing doses of the active ingredient of 40 mg and 60 mg (as base) in tablets and capsules per day in healthy volunteers demonstrated a favorable safety profile and good tolerability of the active ingredient of this invention and drug in general. In the study, almost no adverse events (AEs) associated with taking the drug were detected (Examples 7-9).

A randomized double-blind placebo-controlled trial (Example 9) of the efficacy and safety of the novel pharmaceutical composition in capsules containing the active ingredient of this invention on 129 patients with GTR (Group 1: 43 patients, active ingredient daily dose: 60 mg (as base A); Group 2: 43 patients, active ingredient daily dose: 40 mg (as base A), and Group 3: 43 patients, placebo) demonstrated high efficacy (Table 2) including on the Hamilton anxiety scale (HARS) (Table 3) and on the Hamilton depression scale (HAMD) (Table 4), as well as on the visual analog scale (VAS) (Table 5), clinical global impression-severity scale (CGI-S) (Table 6), and clinical global impression-improvement scale (CGI-I) (Table 7).

TABLE 2

Response rate to therapy at week 8 of a Modified
Intent-To-Treat (MITT) population of 125 patients

|  | Dose:* 60 mg Number of patients: 42 (N = 42) | | Dose:* 60 mg Number of patients: 40 (N = 40) | | Placebo Number of patients: 43 (N = 43) | |
|---|---|---|---|---|---|---|
|  | Percentage X (%) | Number of patients Y | Percentage X (%) | Number of patients Y | Percentage X (%) | Number of patients Y |
| Patients who attained a 50% HARS total score reduction at Week 8 | 20 (47.6%) | 42 | 22 (55.0%) | 40 | 5 (11.6%) | 43 |
| p value in comparison with placebo-treated patients | 0.00067 | | <0.001 | | | |
| Desired response rate | ≥17 (43.6%) | 39 | ≥17 (43.6%) | 39 | <17 (43.6%) | 39 |

*NaSSA hydrochloride dose in the drug.

TABLE 3

Assessment of changes in the patient's condition using HARS after 8 weeks

| Statistics | Dose:* 40 mg Number of patients: 42 N** = 42 | Dose: 60 mg Number of patients: 44 N = 44 | Placebo, Number of patients: 43 N = 43 |
|---|---|---|---|
| Average per Week 0 | 26.9 | 26.5 | 26.9 |
| Average change (CO**) | −13.4 (1.37) | −12.9 (1.37) | −7.1 (1.39) |
| Confidence interval 95% | [−16.4; −10.5] | [−15.8; −9.91] | |
| Change relative to placebo | −6.9 | −6.4 | |
| p value (relative to placebo) | <0.001 | 0.0001 | |

*NaSSA hydrochloride dose in the drug.
**Standard error.

TABLE 4

Assessment of changes in the patient's condition using HAMD after 8 weeks

| Statistics | Dose:* 40 mg Number of patients: 42 N** = 42 | Dose: 60 mg Number of patients: 44 N = 44 | Placebo, Number of patients: 43 N = 43 |
|---|---|---|---|
| Average per Week 0 | 10.9 | 10.9 | 10.7 |
| Average change (CO**) | −5.2 (0.57) | −4.4 (0.56) | −2.3 (0.58) |
| Confidence interval 95% | [−6.4; −3.9] | [−5.6; −3.2] | |
| Change relative to placebo | −2.92 | −2.14 | |
| p value (relative to placebo) | <0.0001 | 0.0030 | |

*NaSSA hydrochloride dose in the drug.
**Standard error.

TABLE 5

Assessment of changes in the patient's condition using VAS after 8 weeks

| Statistics | Dose:* 40 mg Number of patients: 42 N** = 42 | Dose: 60 mg Number of patients: 44 N = 44 | Placebo, Number of patients: 43 N = 43 |
|---|---|---|---|
| Average per Week 0 | 24.1 | 27.4 | 24.9 |
| Average change (CO**) | −9.5 (3.24) | −11.1 (3.23) | −10.1 (3.29) |
| Confidence interval 95% | [−16.5; −2.6] | [−18.1; −4.2] | |
| Change relative to placebo | 0.59 | −1.03 | |
| p value (relative to placebo) | 0.984 | 0.951 | |

*NaSSA hydrochloride dose in the drug.
**Standard error.

TABLE 6

Assessment of changes in the patient's condition using CGI-S after 8 weeks

| Statistics | Dose:* 40 mg Number of patients: 42 N** = 42 | Dose: 60 mg Number of patients: 44 N = 44 | Placebo, Number of patients: 43 N = 43 |
|---|---|---|---|
| Average per Week 0 | 4.24 | 4.28 | 4.28 |
| Average change (CO**) | −1.34 (0.19) | −1.21 (0.19) | −0.73 (0.19) |
| Confidence interval 95% | [−1.76; −0.92] | [−1.63; −0.79] | |
| Change relative to placebo | −0.61 | −0.48 | |
| p value (relative to placebo) | 0.0077 | 0.0482 | |

*NaSSA hydrochloride dose in the drug.
**Standard error.

TABLE 7

Assessment of changes in the patient's condition using CGI-I after 8 weeks

| Statistics | Dose:* 40 mg Number of patients: 42 N** = 42 | Dose: 60 mg Number of patients: 44 N = 44 | Placebo, Number of patients: 43 N = 43 |
|---|---|---|---|
| Average per Week 0 | 4.00 | 4.03 | 4.02 |
| Average change (CO**) | −1.63 (0.14) | −1.68 (0.14) | −0.80 (0.15) |
| Confidence interval 95% | [−1.93; −1.33] | [−1.99; −1.38] | |
| Change relative to placebo | −0.83 | −0.88 | |

TABLE 7-continued

Assessment of changes in the patient's condition using CGI-I after 8 weeks

| Statistics | Dose:* 40 mg Number of patients: 42 N** = 42 | Dose: 60 mg Number of patients: 44 N = 44 | Placebo, Number of patients: 43 N = 43 |
|---|---|---|---|
| p value (relative to placebo) | 0.0003 | 0.0001 | |

*NaSSA hydrochloride dose in the drug.
**Standard error.

FIGS. 1-5 show the dynamics of changes in the total score on the studied scales during the MITT study, including 125 people, also confirming the high efficacy of the novel pharmaceutical composition in capsules comprising the active ingredient of this invention.

The above-mentioned clinical study of the active ingredient of this invention demonstrated its favorable safety profile and good tolerability in patients (Table 8). The 40-mg dose is close to placebo in terms of safety. At a dose of 60 mg, some side effects were observed, namely: headache, drowsiness, dizziness, weakness, nausea, increased anxiety.

TABLE 8

Adverse events observed in patients in a clinical study of the novel pharmaceutical composition in capsules containing the active ingredient of this invention.

| Adverse effect | Dose:* 40 mg/day, Number of patients: 42 N** = 42 | | Dose: 60 mg/day, Number of patients: 44 N = 44 | | Placebo, Number of patients: 43 N = 43 | |
|---|---|---|---|---|---|---|
| | N | % | N | % | N | % |
| Headache | 2 | 4.8% | 6 | 13.6% | 3 | 7.0% |
| Sleepiness | 1 | 2.4% | 7 | 15.9% | 1 | 2.3% |
| Dizziness | 0 | 0.0% | 4 | 9.1% | 0 | 0.0% |
| Weakness | 0 | 0.0% | 3 | 6.8% | 1 | 2.3% |
| Nausea | 0 | 0.0% | 2 | 4.5% | 0 | 0.0% |
| Increased psychic tension | 0 | 0.0% | 2 | 4.5% | 0 | 0.0% |
| Insomnia | 1 | 2.4% | 0 | 0.0% | 0 | 0.0% |
| Daytime drowsiness | 1 | 2.4% | 0 | 0.0% | 0 | 0.0% |
| Constipation | 0 | 0.0% | 1 | 2.3% | 0 | 0.0% |
| Low hemoglobin level | 1 | 2.4% | 0 | 0.0% | 0 | 0.0% |
| Nocturnal awakening | 0 | 0.0% | 1 | 2.3% | 0 | 0.0% |
| Elevated creatinine kinase level | 0 | 0.0% | 1 | 2.3% | 0 | 0.0% |
| Tingling in the hands | 0 | 0.0% | 1 | 2.3% | 0 | 0.0% |
| Jaw reduction | 0 | 0.0% | 1 | 2.3% | 0 | 0.0% |
| Decreased appetite | 1 | 2.4% | 0 | 0.0% | 0 | 0.0% |
| Impaired concentration | 0 | 0.0% | 1 | 2.3% | 0 | 0.0% |
| Bitter taste in mouth, pain in the left hypochondrium | 0 | 0.0% | 1 | 2.3% | 1 | 2.3% |
| Tension in the body (back, arms, legs) | 0 | 0.0% | 1 | 2.3% | 1 | 2.3% |

*The dose of 2,8-dimethyl-5-(2-phenylethyl-2,3,4,5-tetrahydro-1H-pyrido[4,3-b]indole (1) hydrochloride in the NaSSA pharmaceutical composition.
**Number of people.

This invention is illustrated with the following drawings:

FIG. 1 Dynamics of changes in the overall score on the HARS scale during the study of MITT consisting of 125 patients.

Figure 2:
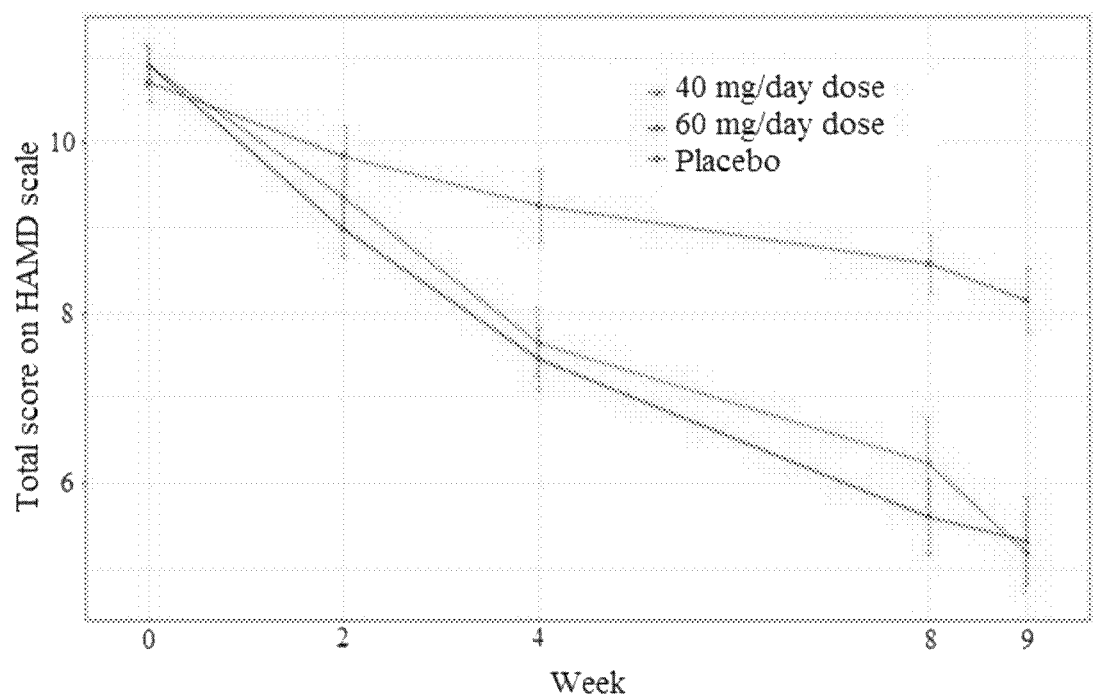

FIG. 2 Dynamics of changes in the overall score on the HAMD scale during the study of MITT consisting of 125 patients.

Figure 3:
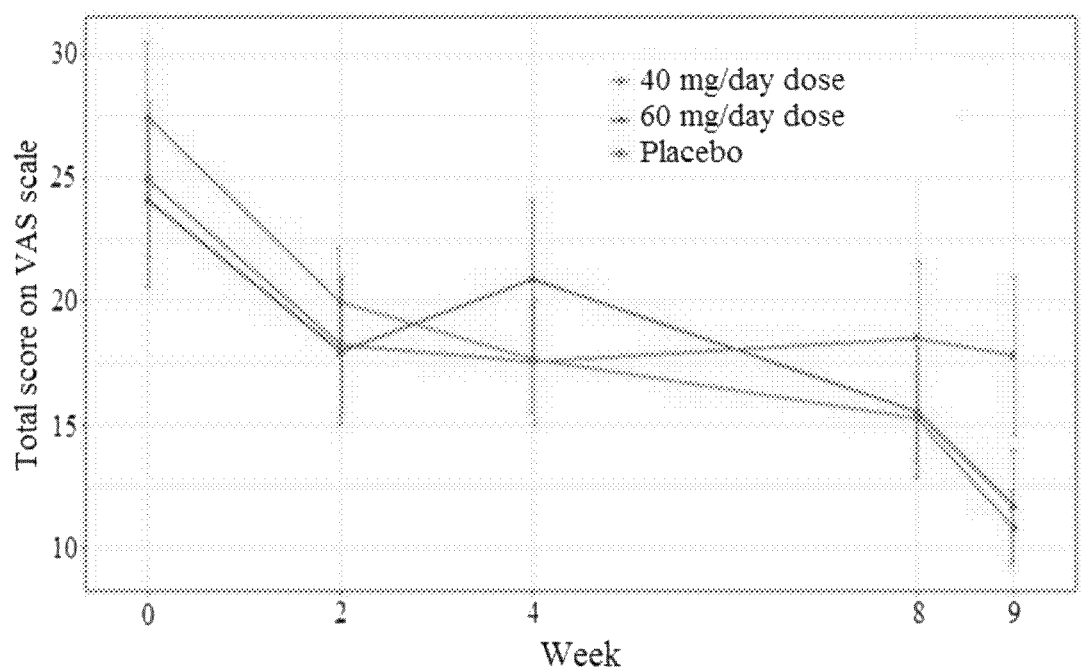

FIG. 3 Dynamics of changes in the overall score on the VAS scale during the study of MITT consisting of 125.

Figure 4:
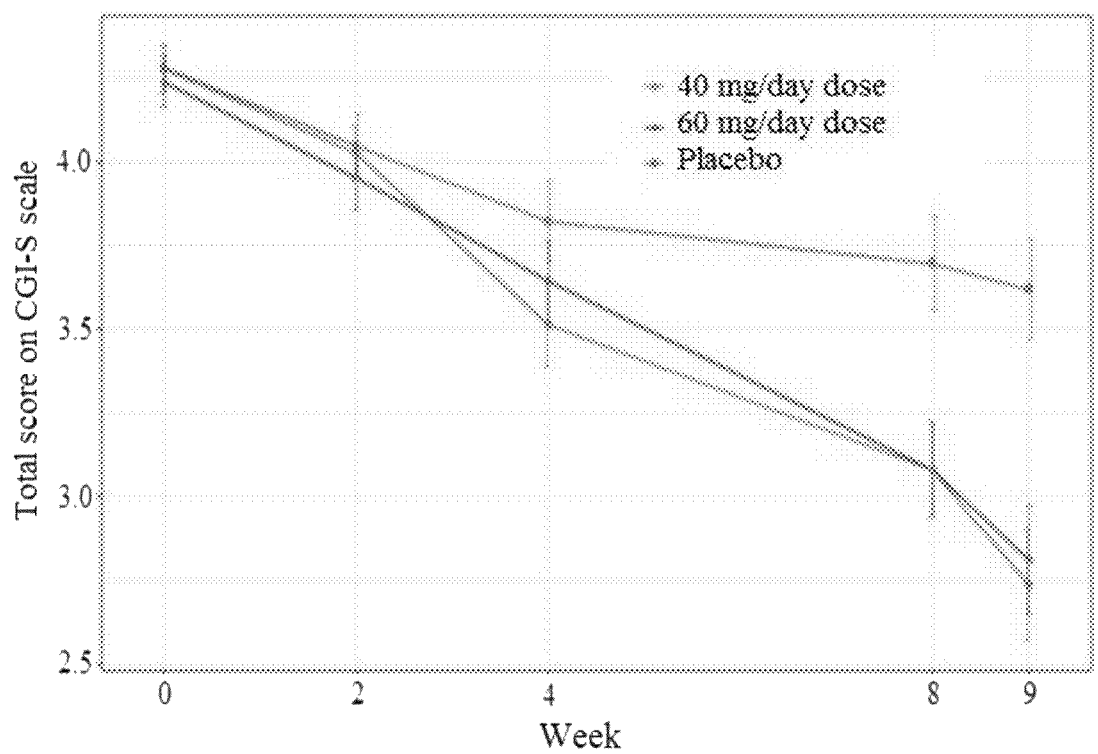

FIG. 4 Dynamics of changes in the overall score on the CGI-S scale during the study of MITT consisting of 125 patients.

Figure 5:
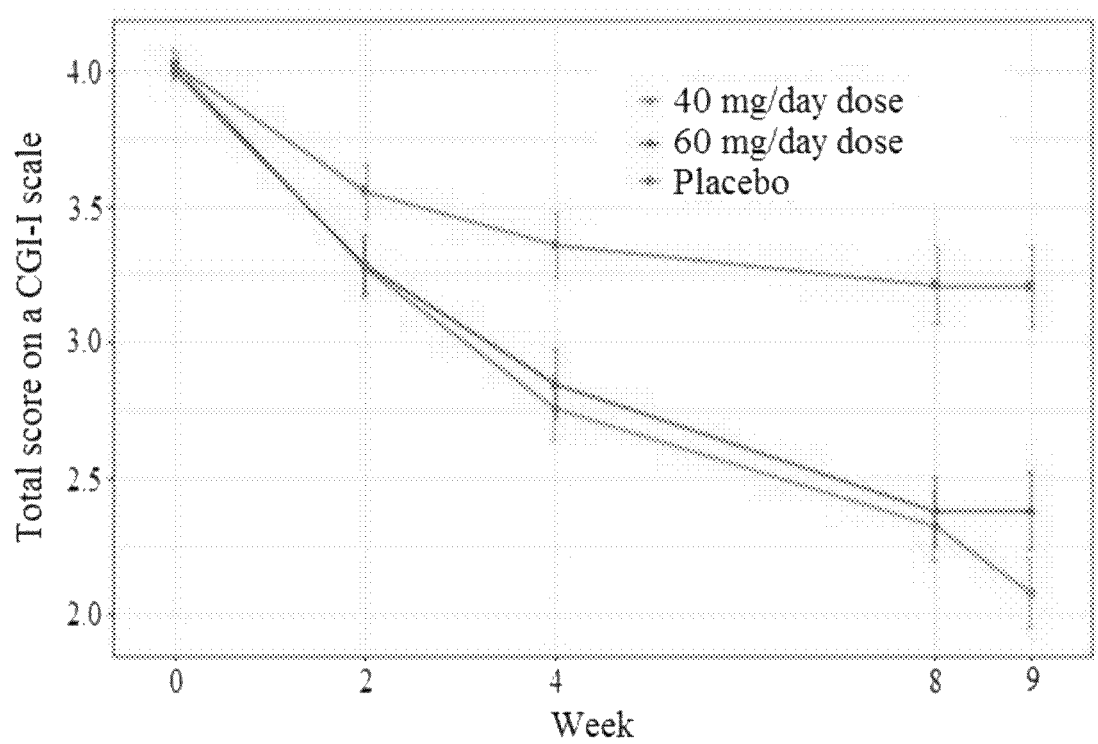

FIG. 5 Dynamics of changes in the overall score on the CGI-I scale during the study of MITT consisting of 125 patients.

Figure 6:
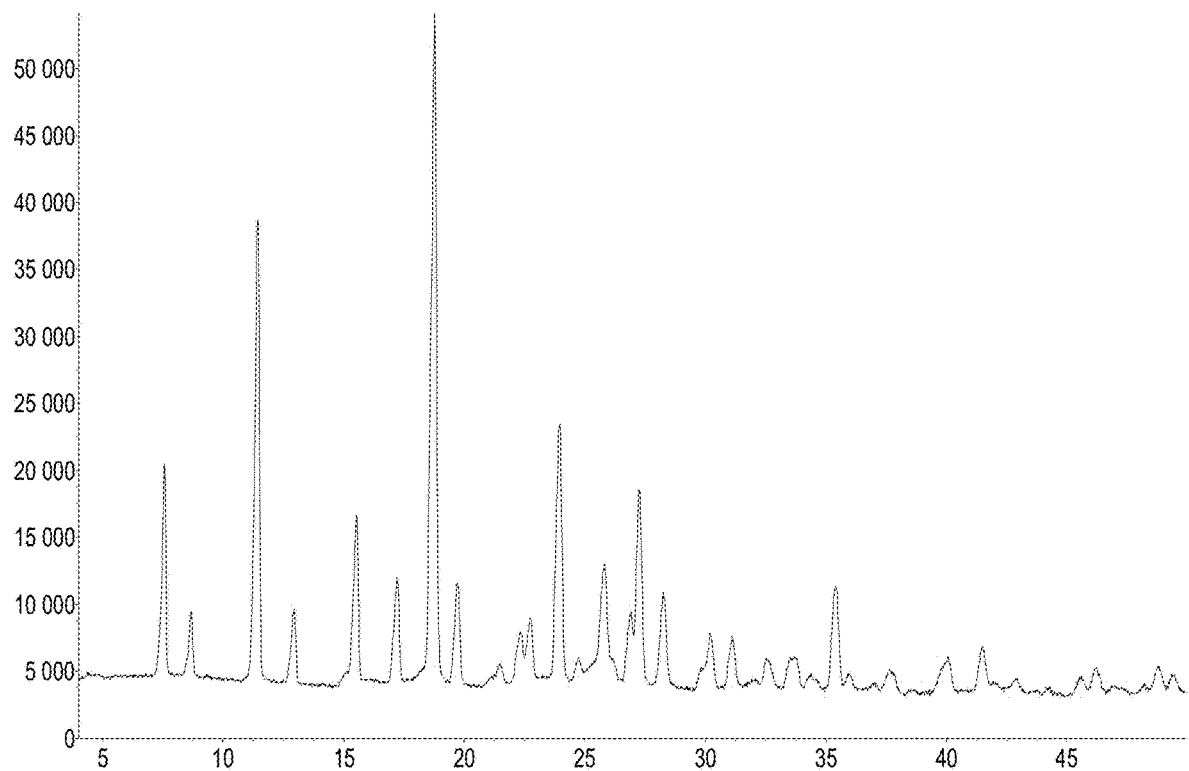

FIG. 6. Diffractogram of A·HCl sample No 021119A prepared according to Example 2 by recrystallization from a hydrochloric acid-water mixture in the ratio 1:12.5.

Figure 7:
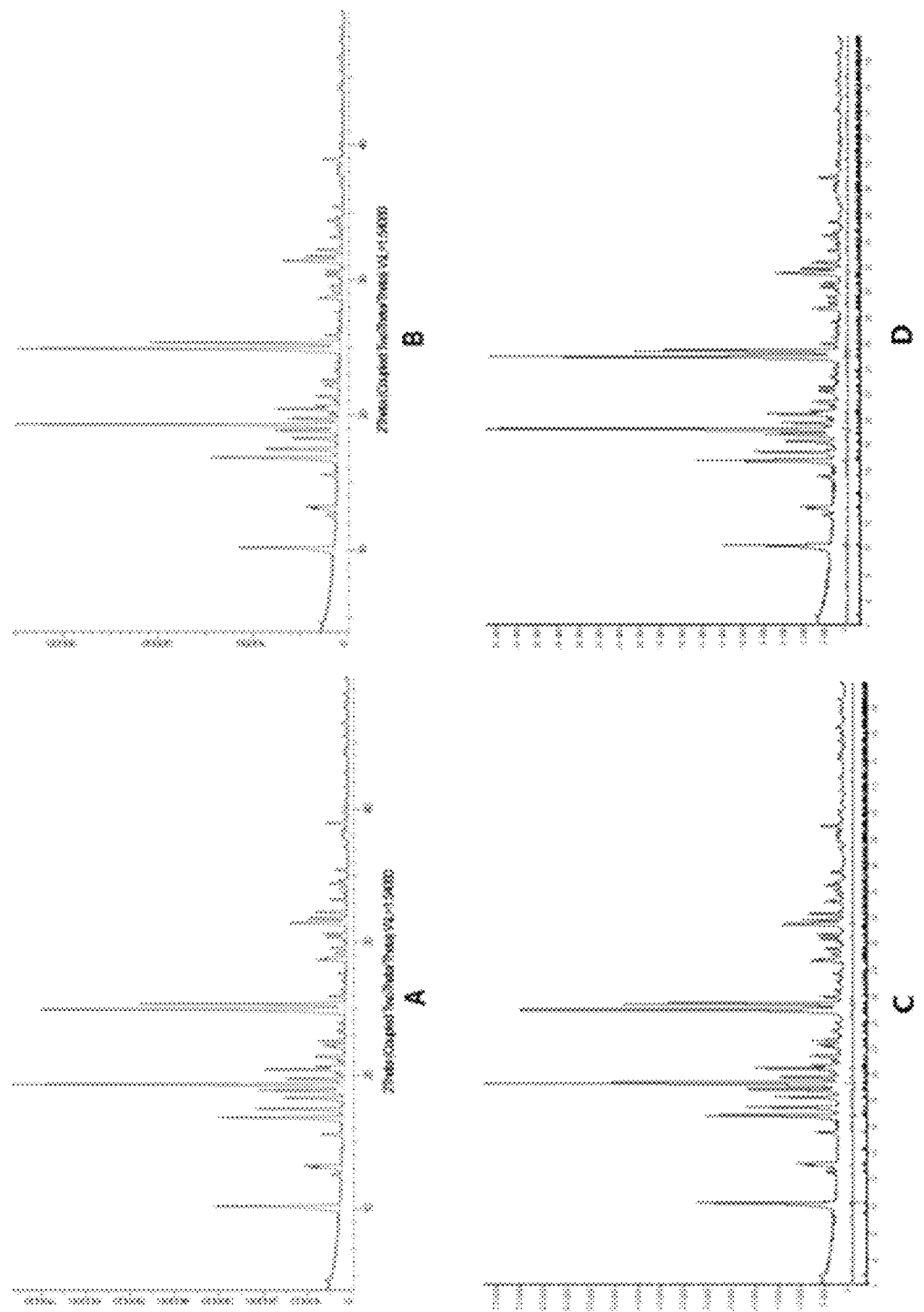

FIG. 7. General view of diffractograms for A·HCl samples Nos 0050120 (A) and 050120MP (B) and theoretical (red line) and experimental (blue line) diffractograms for A·HCl samples Nos 050120 (C) and 050120MP (D) prepared according to Example 4 by recrystallization from isopropanol, and their difference (gray line).

Figure 8:
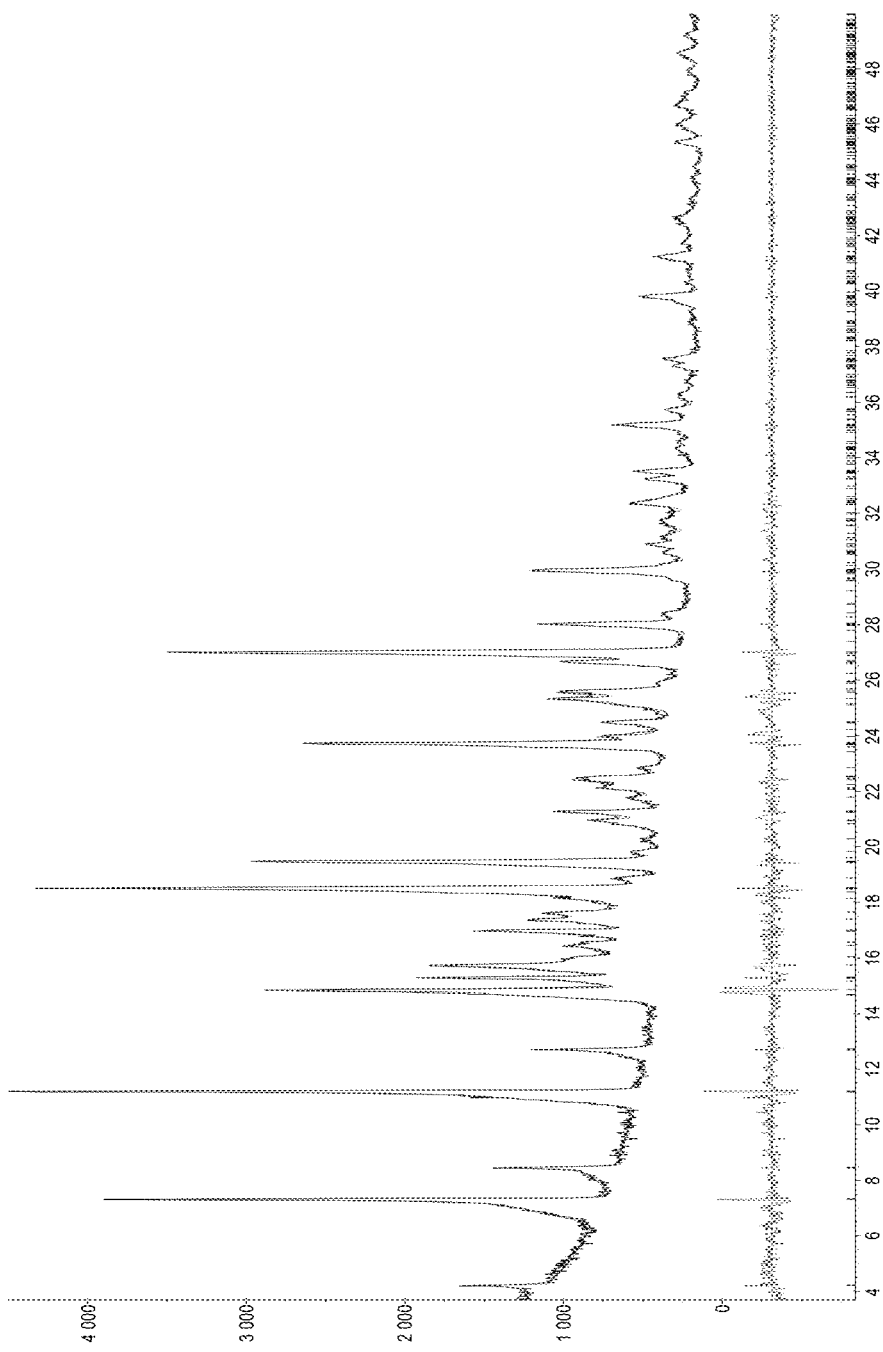

FIG. 8. Theoretical and experimental (red and blue lines) diffractograms for A·HCl crystalline sample No 041119A prepared according to Example 5 by recrystallization from ethanol, and their difference (gray line).

Figure 9:
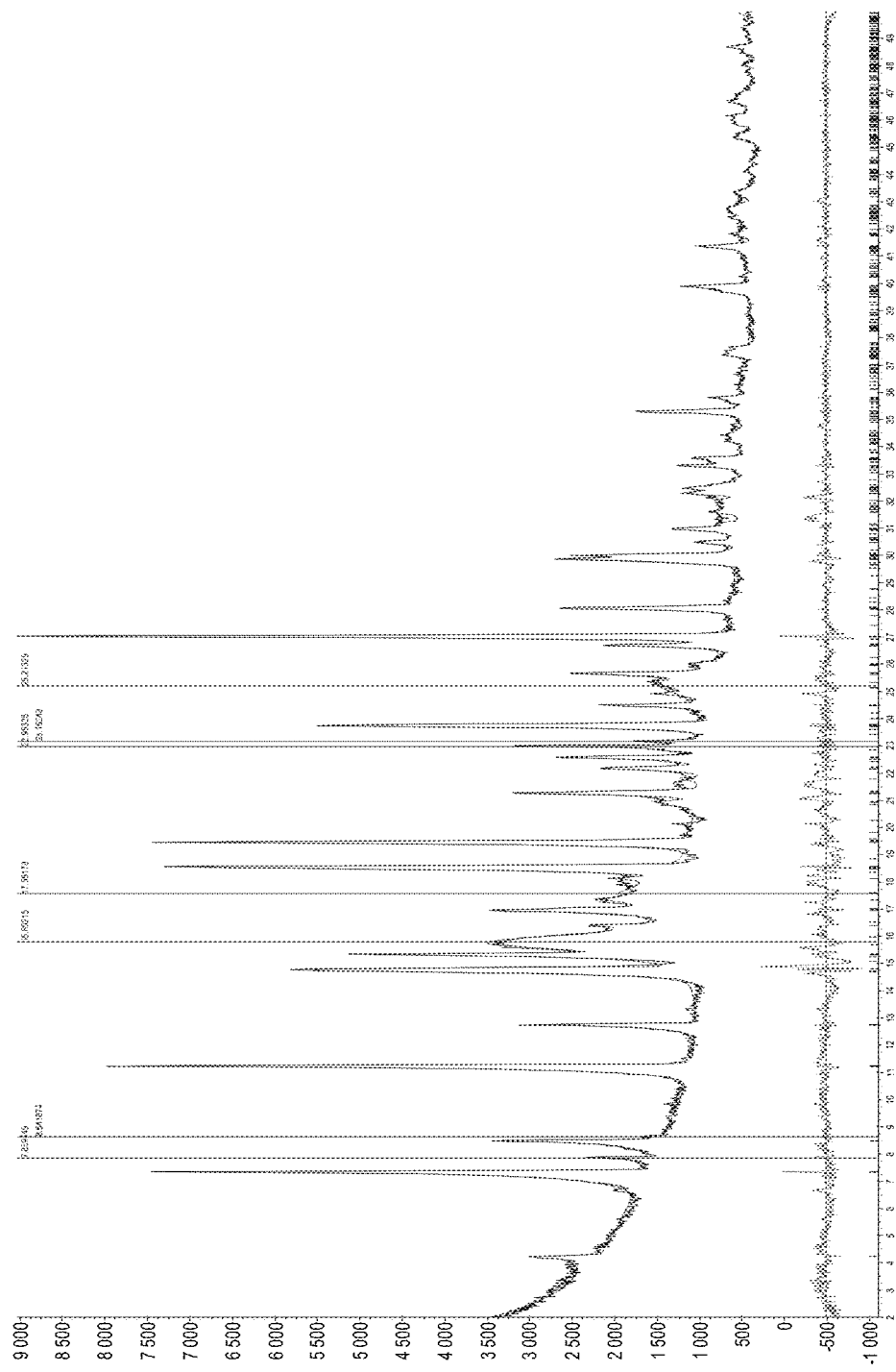

FIG. 9. Theoretical and experimental (red and blue lines) diffractograms for A·HCl sample No 111611 and their difference (gray line). The blue vertical lines represent the positions of impurity peaks.

PREFERRED EMBODIMENT

The following examples will illustrate this invention without limiting it.

Example 1. Synthesis of 2,8-dimethyl-5-(2-phenylethyl)-2,3,4,5-tetrahydro-1H-pyrido[4,3-b]indole hydrochloride (A·HCl). 4-Methylphenylhydrazine hydrochloride (A1 HCl) (2230 g, 14 mol) is charged into a 20-liter reactor, then water (6 l) and methyl tertiary butyl ether (6 l) are added. To the resulting suspension, sodium hydroxide (843 g, 21 mol) is added portionwise while stirring. The mixture is stirred for 40 min until the initial hydrochloride is completely dissolved, the stirring is stopped, and the mixture is delaminated. The lower water layer is drained through the bottom tap. The heating is switched on to distill methyl tertiary butyl ether (5 l) off. The heating is then switched off, and dimethylsulfoxide (1.4 l), hexane (2.1 l), potassium hydroxide pre-triturated in a mortar (39 g, 0.7 mol), and 2196 g (21 mol) of styrene (A6) are added to the cooled reaction mass while stirring. The reaction mass is heated to boiling and boiled with a Dean-Stark nozzle 20-30 h. Upon completion of the reaction (disappearance of the initial) (A1·HCl), TLC control), the heating is switched off and then stirring is stopped. Water (5-7 volumes) is added to the cooled reaction mass and the mixture is extracted with methyltretbutyl ether (3×5 l). The combined organic fractions are filtered through celite (281 g) and concentrated in vacuum on a rotary evaporator. Concentrated hydrochloric acid (1.27 l) is carefully added to the residue at intensive stirring, and the resulting precipitate is transferred to the filter, washed with hexane (4.2 l), and dried to yield 2600 g of 1-(4-methylphenyl)-1-(2-phenethyl)hydrazine hydrochloride (A7·HCl) (70%). $^1$H NMR (400 MHz, DMSO) δ md=10.54 (s, 3H), 7.35-7.04 (m, 9H), 3.78-3.61 (m, 2H), 2.85-2.71 (m, 2H), 2.28 (s, 3H).

Example 2. Synthesis of 2,8-dimethyl-5-(2-phenylethyl)-2,3,4,5-tetrahydro-1H-pyrido[4,3-b]indole hydrochloride (A·HC). In a 100-liter reactor, 10 g of 1-(4-methylphenyl)-1-(2-phenethyl)hydrazine hydrochloride (A7·HCl) and 5.5 g N-methylpiperidone-4 (A2) are mixed in ethanol (20 ml). The resulting mixture is stirred until completely dissolved, concentrated hydrochloric acid (10 ml) is gradually added, and the reaction mixture is boiled for 4-6 h, with the process of the reaction controlled by TLC. After the complete conversion of A7·HCl, the heating is switched off and water (125 ml) is added. The stirring is stopped, and the reaction mixture is left at room temperature. The precipitated crystals were filtered off and air dried to give 12 g of the target product A·HCl (88%). $^1$H NMR (400 MHz, DMSO) δ md=11.23 (s, 1H), 7.38 (d, J=8.3 Hz, 1H), 7.31-7.16 (m, 4H), 7.11 (d, J=6.9 Hz, 2H), 6.98 (d, J=8.1 Hz, 1H), 4.81-3.88 (m, 4H), 3.57 (s, 1H), 3.35 (s, 1H), 3.13-2.78 (m, 6H), 2.67 (s, 1H), 2.38 (s, 3H). The resulting product A·HCl (sample No 021119A) was studied by x-ray phase method on a Bruker D8 Advance diffractometer equipped with a germanium monochromator and a system of slits for monochromatizing and focusing (λ.[CuKα]=1.5406 Å) as well as a position-sensitive LynxEye detector in the angular range from 4° to 500 in 2θ and a step size of 0.02°. Recording was performed by passing X rays through the sample. A 50-mg sample was triturated in a mortar for 1-2 minutes, spread on a mylar film (Chemplex), and a thin layer of the sample was clamped in the sample holder between two films. Then the diffraction pattern was measured for ~4 hours. The resulting diffractogram (FIG. 6) could not be identified, which indicates that the resulting sample is polycrystalline.

Example 3. Synthesis of 2,8-dimethyl-5-(2-phenylethyl)-2,3,4,5-tetrahydro-1H-pyrido[4,3-b]indole hydrochloride (A·Cl). The resulting 1-(4-methylphenyl)-1-(2-phenethyl) hydrazine hydrochloride (A7·HCl) (2500 g, 9.5 mol) is fed into a 100-liter reactor equipped with a mechanical stirrer and ethanol (5 l) and N-methylpiperidone-4 (A2) (1184 g, 10.5 mol) are added. The mixture is stirred to completely dissolve A7·HCl, and concentrated hydrochloric acid (1.24 l) is gradually added. The mixture is heated to a boil and boiled, while the reaction process is controlled by TLC. After 8 hours, a full conversion of A7·HCl was observed. The heating is switched off, the reaction mass is allowed to cool to room temperature, and water (40 l) is added with intensive stirring. After 30-40 minutes, precipitation begins. The reaction mass is left to stir overnight. The stirring is then stopped, and the residue is filtered off, washed with a small amount of water, and dried first in air and then in vacuum to reach a constant mass. The yield is 2987 g of A·HCl (92%).

Example 4. Preparation of 2,8-dimethyl-5-(2-phenylethyl-2,3,4,5-tetrahydro-1H-pyrido[4,3-b]indole hydrochloride (A·HCl) in a crystalline form (CF1). The A·HCl (2987 g) synthesized in Example 3 is dissolved while stirring vigorously and boiling in isopropanol (76.2 l). The heating is stopped, and the reaction mixture is left to stir for 12 h. The resulting crystalline precipitate is filtered off, washed with a small amount of isopropanol, and vacuum dried at a temperature below 50° C. to constant mass to give 2021 g of A·HCl (70%) (crystalline sample No 050120). $^1$H NMR (400 MHz, DMSO) δ md=11.35 (s, 1H), 7.38 (d, J=8.3 Hz, 1H), 7.32-7.15 (m, 4H), 7.11 (d, J=6.8 Hz, 2H), 6.98 (d, J=8.3 Hz, 1H), 4.63-4.02 (m, 4H), 3.56 (s, 1H), 3.29 (s, 1H), 3.09-2.76 (m, 6H), 2.67 (s, 1H), 2.38 (s, 3H). Following the crystallization of A·HCl, the mother liquor is evaporated on a rotary evaporator, and the residue is washed on the filter with isopropyl alcohol (2 l) and air dried to constant mass. The obtained additional product (547 g) is fed into a 30-liter reactor, then isopropyl alcohol (14.5 l) is added, and the mixture is heated to a boil while stirring. The heating is stopped after complete dissolution of the residue. The reaction mixture is left to stir for 12 h. The resulting crystalline precipitate is filtered off, washed with a small amount of isopropanol, and vacuum dried to constant mass at a temperature below 50° C. to yield 383 g (70%) of A·HCl (crystalline sample No 050120MP) identical, according to Claim X-ray phase analysis data, to the original crystalline sample A·HCl No 050120, which corresponds to the rhombic crystallographic group (PM-1) with a cell volume of 3813.4(2) Å$^3$ and the following lattice parameters: a=10.5074(2) Å, b=37.360(2) Å, and c=9.7144(2) Å (FIG. 7, Table 9). Samples were recorded on a Bruker D8 Advance Vario X-ray Powder Diffractometer equipped with a Ge111 monochromator and a LynxEye position-sensitive detector. Recording was performed by passing X rays through a rotating sample clamped between two mylar films. Diffraction patterns were described using TOPAS software.

TABLE 9

Characteristics of the main diffraction maxima of A•HCl samples Nos 0050120 and 050120MP prepared according to Example 4 by recrystallization from isopropanol

| A•HCl sample No 0050120 | | | A•HCl sample No 050120MP | | |
|---|---|---|---|---|---|
| Angle 2θ, ° | d-spacing, Å | Relative intensity, % | Angle 2θ, ° | d-spacing, Å | Relative intensity, % |
| 4.705 | 18.76782 | 1.60% | 4.687 | 18.83795 | 1.10% |
| 9.451 | 9.35063 | 0.70% | 9.407 | 9.39443 | 0.50% |
| 10.238 | 8.63299 | 37.20% | 10.239 | 8.6325 | 29.70% |
| 12.607 | 7.01572 | 3.10% | 12.603 | 7.01794 | 3.10% |
| 13.131 | 6.73699 | 9.20% | 13.125 | 6.73987 | 7.60% |
| 13.261 | 6.67135 | 11.10% | 13.262 | 6.67049 | 9.40% |
| 14.262 | 6.20511 | 0.40% | 14.252 | 6.20955 | 0.30% |
| 15.601 | 5.67557 | 6.40% | 15.601 | 5.67573 | 4.90% |
| 16.846 | 5.25878 | 36.40% | 16.845 | 5.25893 | 39.10% |
| 17.505 | 5.0623 | 25.50% | 17.508 | 5.06124 | 22.70% |
| 18.298 | 4.84452 | 17.40% | 18.296 | 4.84521 | 14.00% |
| 18.885 | 4.69528 | 25.20% | 18.881 | 4.69619 | 19.90% |
| 19.325 | 4.58939 | 100.00% | 19.322 | 4.59001 | 100.00% |

TABLE 9-continued

Characteristics of the main diffraction maxima of A•HCl samples Nos 0050120 and 050120MP prepared according to Example 4 by recrystallization from isopropanol

| A•HCl sample No 0050120 | | | A•HCl sample No 050120MP | | |
|---|---|---|---|---|---|
| Angle 2θ, ° | d-spacing, Å | Relative intensity, % | Angle 2θ, ° | d-spacing, Å | Relative intensity, % |
| 19.762 | 4.48888 | 16.80% | 19.76 | 4.48934 | 15.50% |
| 20.471 | 4.33502 | 23.60% | 20.47 | 4.3351 | 19.50% |
| 20.667 | 4.2942 | 8.20% | 20.651 | 4.2975 | 7.20% |
| 21.421 | 4.14486 | 8.80% | 21.422 | 4.1447 | 7.20% |
| 22.115 | 4.01628 | 4.00% | 22.119 | 4.01563 | 3.00% |
| 22.268 | 3.98913 | 6.40% | 22.256 | 3.99108 | 5.10% |
| 22.592 | 3.93264 | 7.80% | 22.586 | 3.93364 | 6.10% |
| 24.934 | 3.56827 | 90.60% | 24.928 | 3.56911 | 99.80% |
| 25.393 | 3.50478 | 60.90% | 25.389 | 3.50524 | 58.80% |
| 25.955 | 3.43015 | 5.40% | 25.946 | 3.43128 | 5.10% |
| 28.733 | 3.10455 | 7.40% | 28.698 | 3.10817 | 7.70% |
| 30.396 | 2.93833 | 6.10% | 29.199 | 3.05597 | 3.30% |
| 30.661 | 2.91352 | 7.00% | 29.593 | 3.01618 | 4.00% |
| 31.467 | 2.84075 | 17.20% | 30.387 | 2.93923 | 5.40% |
| 31.828 | 2.80935 | 11.40% | 30.655 | 2.91405 | 5.30% |
| 32.281 | 2.77092 | 9.40% | 31.46 | 2.84131 | 18.50% |
| 33.246 | 2.69269 | 5.00% | 31.82 | 2.80998 | 11.30% |
| 34.44 | 2.60197 | 5.30% | 32.283 | 2.77076 | 8.00% |
| 38.945 | 2.31074 | 6.50% | 34.432 | 2.60259 | 5.10% |
| | | | 38.934 | 2.31138 | 6.80% |

Example 5. Preparation of CF2 2,8-dimethyl-5-(2-phenylethyl-2,3,4,5-tetrahydro-1H-pyrido[4,3-b]indole hydrochloride (A·HCl) in a crystalline form (CF2). A·HCl (25 g) is dissolved while stirring vigorously and boiling in ethanol (0.66 l). The heating is stopped, and the reaction mixture is left to stir for 24 h. The resulting precipitate is filtered off, washed with a small amount of isopropanol, and vacuum dried at a temperature below 50° C. to constant mass to give 12.5 g (50%) A·HCl crystalline sample No 041119A). $^1$H NMR (400 MHz, DMSO) δ md=11.39 (s, 1H), 7.37 (d, J=8.3 Hz, 1H), 7.30-7.15 (m, 4H), 7.11 (d, J=6.8 Hz, 2H), 6.98 (d, J=9.2 Hz, 1H), 4.79-3.85 (m, 4H), 3.7-3.19 (m, 2H), 3.17-2.76 (in, 6H), 2.75-2.55 (m, 1H), 2.38 (s, 3H). The obtained crystalline sample No 041119A appears as rhombic crystals characterized by the crystallographic group Pnnn (PM-2) with a cell volume of 6042.4(3) Å$^3$ and the following lattice parameters: a=41.673(8) Å, b=24.107(7) Å, and c=6.0141 (17) Å (FIG. 8, Table 10). Samples were recorded on a Bruker D8 Advance Vario X-ray Powder Diffractometer equipped with a Ge111 monochromator and a LynxEye position-sensitive detector. Recording was performed by passing X rays through a rotating sample clamped between two mylar films. Diffraction patterns were described using TOPAS software.

TABLE 10

Characteristics of the main diffraction maxima of A•HCl sample No 041119A prepared according to Example 5 by recrystallization from ethanol

| Angle 2θ, ° | d-spacing, Å | Relative intensity, % |
|---|---|---|
| 4.207 | 20.985 | 12.60% |
| 7.314 | 12.07753 | 79.80% |
| 8.451 | 10.45497 | 19.10% |
| 11.198 | 7.89513 | 100.00% |
| 12.704 | 6.96248 | 17.70% |
| 14.827 | 5.97005 | 52.70% |
| 15.289 | 5.79058 | 32.00% |
| 15.714 | 5.63507 | 26.70% |
| 16.98 | 5.21759 | 21.30% |
| 17.415 | 5.08804 | 9.50% |
| 17.598 | 5.03559 | 10.90% |
| 18.512 | 4.78913 | 95.70% |
| 19.472 | 4.55509 | 64.00% |
| 20.966 | 4.23378 | 9.90% |
| 21.269 | 4.17411 | 15.70% |
| 22.134 | 4.0128 | 7.30% |
| 22.404 | 3.96507 | 11.30% |
| 23.718 | 3.74828 | 57.30% |
| 23.976 | 3.70864 | 7.40% |
| 24.483 | 3.63294 | 9.00% |
| 25.335 | 3.51262 | 17.20% |
| 25.587 | 3.47862 | 16.40% |
| 26.66 | 3.34098 | 17.90% |
| 27.001 | 3.29961 | 82.40% |
| 28.014 | 3.18254 | 22.70% |
| 29.947 | 2.98138 | 23.50% |
| 30.874 | 2.8939 | 4.10% |
| 32.37 | 2.76347 | 6.80% |
| 33.243 | 2.69289 | 6.40% |
| 33.512 | 2.67192 | 8.50% |
| 35.181 | 2.54889 | 11.00% |
| 39.795 | 2.26332 | 7.40% |

Example 6. Preparation of a polymorphic mixture comprising PM-2 and an amorphous phase. A7·HCl (217 g, 1.92 mol), N-methylpiperidone-4 (394.5 g, 1.74 mol), and ethanol (0.91 l) are mixed together. The mixture is stirred until A7·HCl is completely dissolved, and concentrated hydrochloric acid (370 ml) is added dropwise. The reaction mixture is boiled for 4-6 hours B, while the reaction process is controlled by TLC. The heating is switched off, the reaction mass is allowed to cool to room temperature, and water (8 l) is added with intensive stirring. After 30-40 minutes, precipitation begins. The reaction mass is left to stir overnight. The stirring is then stopped, and the residue is filtered off, washed with a small amount of water, and dried first in air and then in vacuum to reach a constant mass. The yield of A·HCl (sample No 111611) is 529 g (89%). $^1$H NMR (400 MHz, DMSO-d6) δ 11.19 (bs, 1H), 7.45-7.34 (m, 1H), 7.31-7.15 (m, 4H), 7.14-7.06 (m, 2H), 7.04-6.93 (m, 1H), 4.58-4.09 (m, 4H), 3.68-3.50 (m, 1H), 3.36-3.20 (m, 1H), 3.08-2.79 (m, 6H), 2.74-2.58 (m, 1H), 2.38 (s, 3H). The diffractograms of the resulting sample No 111611 are shown in FIG. 5. The positions of most of the peaks on the diffractogram of sample No 111611 (FIG. 5) and on the diffractogram of sample no 041119A (FIG. 4) are similar, except that sample No 111611 demonstrates several impurity peaks. It is worth noting that these peaks have different widths, suggesting that at least two phases are present in the sample: crystalline (PM-2) and amorphous. The intensity portion of amorphous impurity peaks in the sample is 25%.

Example 7. An oral drug of this invention made as a pharmaceutical composition in tablets. The active ingredient of this invention pre-sieved on a vibrating screen were mixed in a high-shear mixer and then pressed into a bar. The resulting bar was crushed into granules and sifted through a sieve to collect granules of 14-16 mesh size. The granules obtained in this way were pressed into the form of double concave tablets, which were coated with a water-based acrylic enteric delayed-release film Colorcon Acryl-EZE. The resulting oral drug of this invention (Table 11) in the form of tablets was used further in clinical studies.

TABLE 11

Compositions of the oral drug of this invention made as a pharmaceutical composition in tablets comprising 2 mg or 10 mg (as A base) of the active ingredient of this invention

|  | 2-mg tablet | | 10-mg tablet | |
|---|---|---|---|---|
| Component | mg | % | mg | % |
| Active ingredient of this invention (as A base) | 2.24 (2.0) | 2.2 (2.00) | 11.2 (10.0) | 11.1 (10.0) |
| Microcrystalline cellulose 101 | 43.5 | 43.4 | 40.5 | 40 |
| Lactose monohydrate 200 | 50 | 49.9 | 45 | 44.4 |
| Colloidal silicon dioxide (Aerosil) | 1 | 1 | 1 | 1 |
| Polyvinylpyrrolidone | 2.5 | 2.5 | 2.5 | 2.5 |
| Calcium stearate | 1 | 1 | 1 | 1 |
| Total | 100.24 | 100 | 101.2 | 100 |

Example 8. An oral drug of this invention made as a pharmaceutical composition in capsules. The active ingredient of this invention, microcrystalline cellulose 101, lactose monohydrate 200, colloidal silicon dioxide (Aerosil), calcium stearate, polyvinylpyrrolidone and starch sodium glycolate are sifted on a vibrating screen (the diameter of the sieve cells is 0.5 mm). The sifted components are weighed in separate containers in the required ratio. Microcrystalline cellulose and hydrochloride (A·HCl) are loaded into a high-shear mixer and stirred 60 seconds at the rotation speed of the main agitator 350±100 rpm and the rotation speed of the chopper 900±100 rpm. After 60 seconds, lactose monohydrate 200 is loaded and the stirring is continued at the same parameters for another 60 seconds. Then, silicon dioxide colloidal, polyvinylpyrrolidone, and sodium starch glycolate are loaded one by one, with stirring continued after loading each component at the same parameters for 60 seconds. Then, calcium stearate is loaded and stirred for 40 seconds at the rotation speed of the main agitator 2001100 rpm. The resulting pharmaceutical composition is encapsulated on a capsule machine in capsules No 4 with a white body and cap to produce an oral drug of this invention made as a pharmaceutical composition in capsules (Table 12), which was further used in clinical studies.

Example 9. An oral drug of this invention made as a pharmaceutical composition in capsules. Anhydrous lactose, potato starch 6%, and hydrogenated castor oil (Kolliwax HCO) are weighed in separate containers and sifted on a vibrating screen (sieve cell diameter=0.5 mm). The sifted components are weighed in separate containers. Then, A·HCl in crystalline form I or II, anhydrous lactose, and potato starch 6% are loaded into a tumble barrel mixer, where the mixture is stirred for 15 minutes. Then, hydrogenated castor oil is added and the mixture is stirred for another 3 minutes. The resulting pharmaceutical composition is fed into a roller compactor and compacted at a feeder speed of 20±10 rpm, a pressure of 25±5 kN, a roller rotation speed of 8±2 rpm, a calibrator rotation speed of 150±50 rpm, and a calibrator cell diameter of 0.6 mm. The resulting granulate of the pharmaceutical composition is sifted on a vibrating screen through a screen with a cell diameter of 0.5 mm.

The sieved granulate of the pharmaceutical composition is loaded into a tumble barrel mixer and stirred for 5 minutes, whereupon encapsulated on a capsule machine in capsules No4 with a white body and cap. As a result, an oral drug of this invention is produced as a pharmaceutical composition in capsules, which was further used in clinical studies. Table 13 summarizes the ingredients of said oral drug.

TABLE 13

The ingredients of the oral drug of this invention made as a pharmaceutical composition in capsules, each containing 22.4 mg of the active ingredient of this invention, or 20 g of base A

|  | Content | |
|---|---|---|
| Components | mg | % |
| Active ingredient of this invention (as A•HCl) | 22.400 (20.000) | 12.4 (11.1) |
| Anhydrous lactose (Lactopress ® Anhydrous) | 152.20 | 85.6 |
| Potato starch 6% | 4.50 | 2.5 |
| Hydrogenated castor oil (Kolliwax HCO) | 0.90 | 0.5 |
| Total | 180.0 | 100.0 |

Example 10. Clinical study of the safety of the oral drug of this invention. An open-label clinical trial of the pharmacokinetics of the antipsychotic drug made as a pharmaceutical composition of this invention in capsules, was conducted with a single oral administration in 32 healthy volunteers at doses of 2 mg/day (cohort 1, 8 volunteers), 4 mg/day (cohort 1, 8 volunteers), 10 mg/day (cohort 1, 8

TABLE 12

Compositions of the oral drug of this invention made as a pharmaceutical composition capsules comprising 2 mg, 10 mg, or 20 mg (as A base) of the active ingredient of this invention

|  | 2-mg capsule | | 10-mg capsule | | 20-mg capsule | |
|---|---|---|---|---|---|---|
| Component | mg | % | mg | % | mg | % |
| Active ingredient of this invention (as A base) | 2.24 (2.0) | 2.2 (2.00) | 11.2 (10.0) | 11.1 (10.0) | 22.40 (20.0) | 17.2 (20.0) |
| Microcrystalline cellulose 101 | 41.4 | 41.30 | 41.4 | 40.9 | 53.0 | 40.8 |
| Lactose monohydrate 200 | 44.0 | 43.90 | 36.0 | 35.6 | 52.65 | 40.5 |
| Colloidal silicon dioxide (Aerosil) | 2.8 | 2.80 | 2.8 | 2.8 | 0.65 | 0.5 |
| Polyvinylpyrrolidone | 4.2 | 4.2 | 4.2 | 4.1 | — | — |
| Sodium starch glycolate | 4.2 | 4.2 | 4.2 | 4.1 | — | — |
| Calcium stearate | 1.4 | 1.4 | 1.4 | 1.4 | | |
| Magnesium stearate | — | — | — | — | 1.30 | 1.0 |
| Total | 100.24 | 100 | 101.2 | 100 | 130 | 100 | volunteers), and 20 mg/day (cohort 1, 8 volunteers), expressed as base A, in accordance with the recommendations of "Good clinical practice (GCP)" on physically and mentally healthy men aged 20-50 years with a body mass index of 20-55. The results of the trial have demonstrated that the antipsychotic drug made as a pharmaceutical composition of this invention in capsules is well tolerated in single doses of 2, 4, 10, and 20 mg and neither significantly affect the parameters of plasma and urine, nor prolong the QT interval. Side effects like drowsiness, agitation and paresthesia were observed in a 20-mg cohort. The harmonic mean half-life ran up to 14 hours showing a linear increase in $C_{max}$ and AUC in the dose range from 2 to 20 mg, with the maximum concentration in the blood of the base (A) being reached in about an hour (Table 14).

TABLE 14

Average values of pharmacokinetic parameters for 8 volunteers with a single oral dosage of the antipsychotic drug made as a pharmaceutical composition of this invention in capsules

| | Dose as A•HCl | | | | | | | |
|---|---|---|---|---|---|---|---|---|
| | 2 mg | | 4 mg | | 10 mg | | 20 mg | |
| Parameters | Value[a] | Stand. Deviat. SD | Value[a] | Stand. Deviat. SD | Value[a] | Stand. Deviat. SD | Value[a] | Stand. Deviat. SD |
| $C_{max}$, pg/ml | 2.10 | 3.16 | 22.9 | 16.4 | 53.7 | 31.8 | 84.1 | 46.2 |
| $T_{max}$, h | 1.0 | 1-1.5 | 1 | 0.5-1.5 | 0.625 | 0.25-4 | 1 | 0.25-2 |
| $T_{1/2}$, h | 14.1 | 10.2 | 8.15 | 2.23 | 10.2 | 2.55 | 8.18 | 2.09 |
| $AUC_{(0\text{-}inf)}$, pg · h/ml | 94.6 | 26.8 | 211 | 86.2 | 462 | 207 | 834 | 333 |

[a]Value

Example 11. Safety study of increasing doses of the oral drug of this invention made as a pharmaceutical composition of this invention in capsules. Clinical safety study of increasing doses of the antipsychotic drug made as a pharmaceutical composition of this invention in capsules for single and multiple dosing. The study covered one cohort of 4 volunteers taking antipsychotic drug once at a dose of 20 mg, and then at the same dose 2 times a day for 4 days. Based on the three-week safety data obtained in the 20-mg cohort taking antipsychotic drug twice a day, the independent safety data monitoring Committee took a decision to involve a second cohort of 4 volunteers, in which the antipsychotic drug under test was taken once at a dose of 20 mg and then 3 times a day for 4 days at the same dose.

In the study, the antipsychotic drug demonstrated a favorable safety profile and good tolerability. The study did not reveal any adverse events (AEs) associated with taking the drug. AE were observed only in volunteers who received a daily dose of 60 mg. The residual concentration of the antipsychotic drug was stabilized 1-2 days after the start of regular drug administration. The accumulation factor ($F_c$) was 2.5 in the 40-mg cohort and 2.1 in the 60-mg cohort.

For the majority of volunteers, the time of peak concentration of the antipsychotic drug ($T_{max}$) was not pronounced and varied from 0.5 hours to 4 hours, with a median of 0.75 hours in the 40-mg cohort and 2.3 hours in the 60-mg cohort. For repeated doses, the $T_{max}$ variability remains within the same range of 0.3-4 hours, with a median of 0.38 hours μacoB in the 40-mg cohort and 1.0 hour in the 60-mg cohort. $T_{max}$ of the metabolite is observed within the same time frame, suggesting its rapid formation from the source substance.

For a single dose, the average half-life of antipsychotic drug in the 40-mg cohort was 10.3±5.4 hours and in the 60-mg cohort, 7.3±2.6 hours. After repeated administration, there is a tendency to a slight increase in $T_{1/2}$ for most volunteers with 1.4 times on an average.

Example 12. Efficacy and safety study of the oral drug of this invention made as a pharmaceutical composition of this invention in capsules. A multicenter randomized double-blind placebo-controlled study of the efficacy and safety of the antipsychotic drug in people with generalized anxiety disorder (GAD) was conducted for 8 weeks in three cohorts of 43 patients each: a 1-40 mg antipsychotic drug cohort (20 mg×2 times per day); a 2-60 mg antipsychotic drug cohort (20 mg×3 times per day), and a 3-placebo cohort. During the study, 3 scheduled visits were conducted in Week 2, Week 4, and Week 8 to assess the effectiveness and safety of the therapy as well as drug inventory and administration. During all of those visits, the patient's diary was checked, a drug inventory was made and the patients' compliance was assessed. In addition, adverse events, concomitant therapy, and vital signs were evaluated, urine drug screen was performed, and assessments using Hamilton Anxiety Rating Scale (HARS), Hamilton Depression Scale (HAMD), Clinical Global Impression-Severity (CGI-S), Clinical Global Impression-Improvement (CGI-I), and Visual Analog Scale (VAS) were made; women of child-bearing potential will take a urine pregnancy test. Also, during visits at Week 4 and Week 8 a physical examination was performed, body weight was measured, an ECG was performed in 12 leads and blood and urine samples were obtained for laboratory tests, namely: urinalysis and biochemical blood analysis, PK analysis before and 1 hour after taking the study drug (SD), and urinalysis. At Week 4, a blood sample was also obtained for genotyping by CYP2D6. At Week 8, treatment in the groups was completed, and all patients were prescribed a placebo to be taken during the follow-up period, which lasted 1 week. During this time, a possible development of SD withdrawal syndrome against the background of placebo was evaluated. During the visit at Week 9, the patient's diary was checked, a drug inventory was made and the patients' compliance was assessed. In addition, adverse events, concomitant therapy, and vital signs were evaluated, urine drug screen was performed, and assessments using the Hamilton Anxiety Rating Scale (HARS), Hamilton Depression Scale (HAMD), Clinical Global Impression-Severity (CGI-S), Clinical Global Impression-Improvement (CGI-I), and Visual Analog Scale (VAS) were made; women of child-bearing age will take a urine pregnancy test. At this point, the patients' participation in the study was completed, and they received recommendations for further treatment as part of standard GAD therapy.

The main results of the efficacy of the antipsychotic drug in GAD therapy are given in Tables 2-7, and the dynamics of changes in total scores on the Hamilton Anxiety Rating Scale (HARS), Hamilton Depression Scale (HAMD), Clinical Global Impression-Severity (CGI-S), Clinical Global Impression-Improvement (CGI-I), and Visual Analog Scale (VAS) are presented in FIGS. 1-5. These data strongly support the effectiveness of the antipsychotic drug in GAD treatment, including HARS and HAMD data, and its favorable safety profile and good tolerability (Table 8). The 40-mg dose is close to placebo in terms of safety. At a dose of 60 mg, some adverse events are observed like headache, drowsiness, dizziness, weakness, nausea, increased anxiety.

INDUSTRIAL APPLICABILITY

This invention can be used in medicine and veterinary.

The invention claimed is:

1. A pharmaceutical composition comprising a polymorphic form CF1 of 2,8-dimethyl-5-(2-phenylethyl)-2,3,4,5-tetrahydro-1H-pyrido[4,3-b]indole hydrochloride (A·HCl), wherein CF1 exhibits at least X-ray lines (2-theta values) in a powder diffraction pattern when measured using Cu $K_\alpha$ radiation at 10.2±0.2, 16.8±0.2, 19.3±0.2, 24.9±0.2, and 25.3±0.2.

2. A pharmaceutical composition comprising a polymorphic form CF2 of 2,8-dimethyl-5-(2-phenylethyl)-2,3,4,5-tetrahydro-1H-pyrido[4,3-b]indole hydrochloride (A·HCl), wherein CF2 exhibits at least X-ray lines (2-theta values) in a powder diffraction pattern when measured using Cu $K_\alpha$ radiation at 7.3±0.2, 11.2±0.2, 18.5±0.2, 19.5±0.2, and 27.0±0.2.

3. A method for the production of 2,8-dimethyl-5-(2-phenylethyl)-2,3,4,5-tetrahydro-1H-pyrido[4,3-b]indole hydrochloride (A·HCl) by the interaction of 4-methylphenylhydrazine hydrochloride (A1·HCl) with styrene (A6) and subsequent interaction of the resulting methylphenyl)-1-(2-phenylethyl)hydrazine hydrochloride (A7·HCl) with 1-methylpiperidin-4-one (A2) with subsequent transformation of the reaction product (A·HCl) into base (A), if necessary

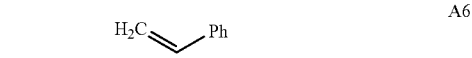

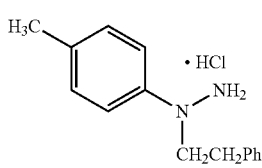

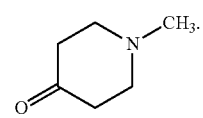

4. A method for the production of a pharmaceutical composition comprising the polymorphic form CF1 of 2,8-dimethyl-5-(2-phenylethyl)-2,3,4,5-tetrahydro-1H-pyrido[4,3-b]indole hydrochloride (A·HCl) of claim 2, comprising recrystallization of 2,8-dimethyl-5-(2-phenylethyl)-2,3,4,5-tetrahydro-1H-pyrido[4,3-b]indole hydrochloride (A·HCl) from isopropanol.

5. A method for the production of a pharmaceutical composition comprising the polymorphic form CF2 of 2,8-dimethyl-5-(2-phenylethyl)-2,3,4,5-tetrahydro-1H-pyrido[4,3-b]indole hydrochloride (A·HCl) of claim 4, comprising recrystallization of 2,8-dimethyl-5-(2-phenylethyl)-2,3,4,5-tetrahydro-1H-pyrido[4,3-b]indole hydrochloride (A·HCl) from ethanol.

6. A method for treating anxiety or depression in humans, comprising administering a pharmaceutical composition of claim 1 or 2 in a therapeutically effective amount.

7. A pharmaceutical formulation selected from the group consisting of tablets, capsules, pills, powders, granules, chewing gums, peroral solutions or suspensions, aerosols, and implants for subcutaneous, intramuscular, intravenous, and intranasal administration, wherein the formulation comprises a pharmaceutically effective amount of at least one of the following pharmaceutical compositions:

a polymorphic form CF1 of 2,8-dimethyl-5-(2-phenylethyl)-2,3,4,5-tetrahydro-1H-pyrido[4,3-b]indole hydrochloride (A·HCl), wherein CF1 exhibits at least X-ray lines (2-theta values) in a powder diffraction pattern when measured using Cu $K_\alpha$ radiation at 10.2±0.2, 16.8±0.2, 19.3±0.2, 24.9±0.2, and a polymorphic form CF2 of 2,8-dimethyl-5-(2-phenylethyl)-2,3,4,5-tetrahydro-1H-pyrido[4,3-b]indole hydrochloride (A·HCl).

8. The pharmaceutical formulation according to claim 7, wherein the formulation is in tablet form containing fillers (lactose and microcrystalline cellulose 101), a free flow agent (Aerosil 200), a suspending agent (polyvinylpyrrolidone), and a lubricant as excipients.

9. The pharmaceutical formulation according to claim 7, wherein the formulation is in capsule form.

10. The pharmaceutical formulation according to claim 8, wherein the tablet is coated with an intestinal-soluble polymer film with delayed release.

11. A method for treatment of anxiety or depression in a patient in need thereof, comprising administering to the patient the pharmaceutical composition according to claim 7, in a therapeutically effective amount.

12. A method for treatment according to claim 11, comprising administering to the patient the pharmaceutical formulation comprising a dose of the active ingredient varying from 2 mg/day to 60 mg/day.

13. The pharmaceutical composition of claim 1, wherein CF1 exhibits at least X-ray lines (2-theta values) in a powder diffraction pattern when measured using Cu $K_\alpha$ radiation at 17.5±0.2, 18.3±0.2, 18.9±0.2, 20.5±0.2, and 31.5±0.2.

14. The pharmaceutical composition of claim 1, wherein CF1 exhibits a cell volume of about 3813 cubic angstroms.

15. The pharmaceutical composition of claim 4, wherein CF1 exhibits the following lattice parameters: a is about 10.5 angstroms, b is about 37.4 angstroms, and c is about 9.7 angstroms.

16. The pharmaceutical composition of claim 2, wherein CF2 exhibits at least X-ray lines (2-theta values) in a powder diffraction pattern when measured using Cu $K_\alpha$ radiation at 14.8±0.2, 15.3±0.2, 15.7±0.2, 23.7±0.2, and 29.9±0.2.

17. The pharmaceutical composition of claim 2, wherein CF2 exhibits a cell volume of about 6042 cubic angstroms.

18. The pharmaceutical composition of claim 2, wherein CF2 exhibits the following lattice parameters: a is about 41.7 angstroms, b is about 24.1 angstroms, and c is about 6.0 angstroms.

* * * * *